(12) United States Patent
Ceravolo

(10) Patent No.: US 11,432,849 B2
(45) Date of Patent: Sep. 6, 2022

(54) PEDICLE SCREW SYSTEM WITH INTEGRATED ROTATIONAL LOCKING MECHANISM

(71) Applicant: Peter C. Ceravolo, Kinnelon, NJ (US)

(72) Inventor: Peter C. Ceravolo, Kinnelon, NJ (US)

(*) Notice: Subject to any disclaimer, the term of this patent is extended or adjusted under 35 U.S.C. 154(b) by 95 days.

(21) Appl. No.: 17/113,426

(22) Filed: Dec. 7, 2020

(65) Prior Publication Data

US 2021/0169530 A1    Jun. 10, 2021

Related U.S. Application Data

(60) Provisional application No. 62/944,584, filed on Dec. 6, 2019.

(51) Int. Cl.
*A61B 17/70* (2006.01)
*A61B 17/86* (2006.01)

(52) U.S. Cl.
CPC ........ *A61B 17/7034* (2013.01); *A61B 17/864* (2013.01); *A61B 2017/8655* (2013.01)

(58) Field of Classification Search
CPC ............ A61B 17/7001; A61B 17/7002; A61B 17/7011; A61B 17/7032; A61B 17/7034; A61B 17/7035; A61B 17/7037; A61B 17/7038; A61B 17/864; A61B 2017/8655

USPC .................. 606/264–267, 269, 272
See application file for complete search history.

(56) References Cited

U.S. PATENT DOCUMENTS 9,655,650 B2 * 5/2017 Blain ................. A61B 17/7002

* cited by examiner

*Primary Examiner* — Eduardo C Robert
*Assistant Examiner* — Christina Negrellirodriguez
(74) *Attorney, Agent, or Firm* — Gearhart Law LLC; David Postolski, Esq.

(57) ABSTRACT

A tulip assembly for use in a pedicle screw system is described. The tulip assembly comprises a ring and a body. A distal end of the body comprises a first and a second reduction channel located on a first and a second side, respectively. A ramp down portion is located between the reduction channel and a securement portion. The securement portions are located distally from the reduction channels. When the tulip assembly is rotated to an open position, the reduction channels receive pins located on a distal end of the ring. Upon applying an axial downward force to a rod within the assembly and rotating the assembly to a closed position, the pins are received and secured by the securement portions. Threads located on an exterior of the body engage threads on an interior of the ring and serve as a locking mechanism to secure the rod in place.

20 Claims, 41 Drawing Sheets

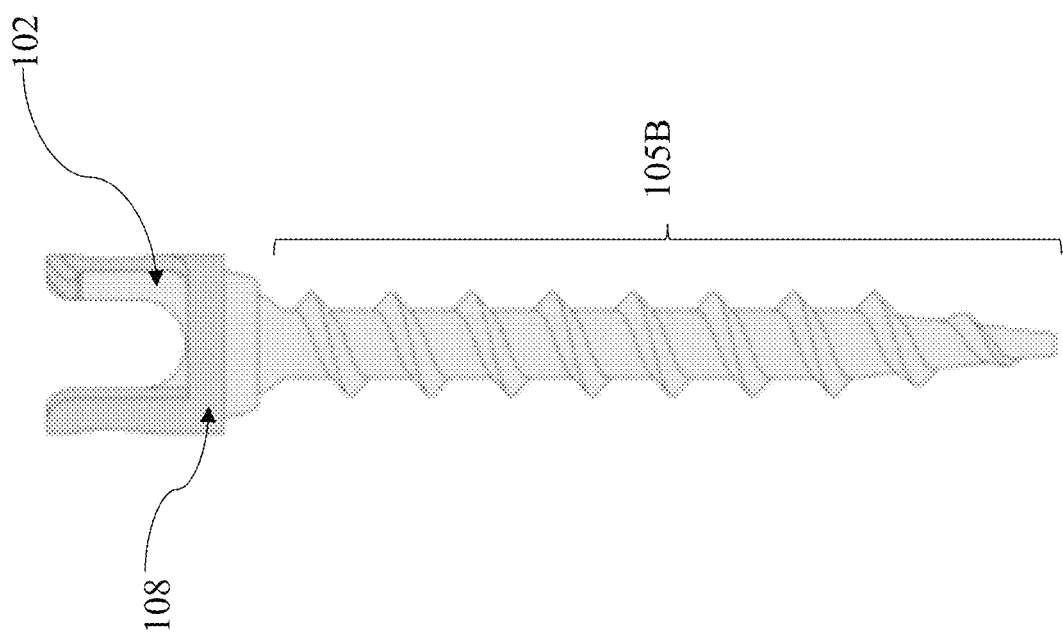

204

PEDICLE SCREW SYSTEM WITH INTEGRATED ROTATIONAL LOCKING MECHANISM

CROSS-REFERENCE TO RELATED APPLICATIONS

This application is a U.S. Non-Provisional patent application that claims priority to U.S. Provisional Patent Application No. 62/944,584, filed on Dec. 6, 2019, the contents of which are hereby fully incorporated by reference.

FIELD OF THE EMBODIMENTS

The field of the invention and its embodiments relate to a pedicle screw system that comprises a pedicle screw and a tulip assembly. In particular, the present invention and its embodiments provide a pedicle screw system that substantially reduces and/or prevents relative motion between spinal segments that are being fused and also provides an integrated locking mechanism to secure the pedicle screw system into a spinal segment region.

BACKGROUND OF THE EMBODIMENTS

The human spinal column or the vertebral column comprises twenty-four separate bones, along with fused bones of the sacrum and coccyx. Specifically, the spinal column includes thirty-three vertebrae, where the upper twenty-four are articulating and separated from each other by intervertebral discs, and the lower nine are fused in adults, with five in the sacrum and four in the coccyx. The spinal column is strong, flexible, and allows a degree of flexible movement in many directions. The spinal column also protects the spinal cord, supports the head, and provides an attachment for the ribs.

Various systems have been designed to provide vertebrae immobilization when needed for the repair of damaged portions of the spine. Typical spinal fixation devices are implanted in the spine or spinal column and are classified as anterior, posterior, or lateral implants. Some systems use spinal fixation assemblies. The spinal fixation assemblies generally include pedicle screw systems. A typical pedicle screw system may include a pedicle screw and a separate locking cap or set screw to secure the rod in place. The pedicle screw may include a distal stem or a body portion affixed to a proximal head portion. As an example, the pedicle screw may be used in a spinal fusion surgery to add enhanced support and strength to the fusion while it heals. Generally, two pedicle screws may be inserted into respective vertebrae and adjusted to distract and/or stabilize the spinal column.

The device may be a tulip assembly, in examples, and may be coupled to the proximal head portion of the pedicle screw. The device may be configured to receive and secure a cylindrical rod. The cylindrical rod connects the pedicle screws between the various vertebrae, which prevents movement and allows for healing.

However, pedicle screw systems known in the technical field have numerous drawbacks. For example, in the typical system, the pedicle screw does not, by itself, fixate the spinal segment, but operates as an anchor point to receive the device, which then receives the cylindrical rod. Moreover, some pedicle screw systems are large and bulky, which may result in tissue damage in and around the surgical site when the pedicle screw system is installed during surgery. Further, the varying size of adjacent vertebrae and the often misalignment of vertebrae causes the pedicle screw placed in substantially consistent portions of the vertebrae structure to not be linearly aligned.

Thus, a need exists for a pedicle screw system that substantially reduces and/or prevents relative motion between spinal segments that are being fused and also provides an integrated locking mechanism to secure the pedicle screw system into a spinal segment region.

Review of Related Technology

U.S. Pat. No. 8,016,866 B2 describes a tulip assembly configured to be coupled to a head of a bone fixation device. The bone fixation devices includes at least one inner member configured to fix the tulip assembly to the head of the bone fixation device and an outer member including at least one engagement surface configured to selectively fix a rod in the tulip assembly via rotation of the outer member.

U.S. Pat. No. 8,142,481 B2 describes pedicle screw system that may be used for fixation of spinal segments and may be used when minimally invasive surgery (MIS) techniques are employed. The pedicle screw system includes a tulip assembly comprising of a tulip body, an inner member, and an expansion member. Installation of the pedicle screw system into pedicles of the spine, for example, includes inserting the pedicle screw into a portion of the spine and then coupling the tulip assembly to the pedicle screw. The tulip assembly may be locked onto the pedicle screw before a distraction rod is placed in the tulip assembly. After the rod is placed in the tulip assembly, the tulip body and the inner member can be rotated relative to one another to lock the rod into the tulip assembly. In addition, the relative rotation may also provide additional locking of the tulip assembly to the pedicle screw.

U.S. Published Patent Application No. 2010/0004693 A1 describes a spine stabilization device that may include a rod and bone fastener assemblies. Each bone fastener assembly may include a bone fastener and a collar. Each bone fastener may have a threaded shank and a head. Each collar may have a first end with a cavity for accommodating the bone fastener and a second end having a channel for accommodating the rod. The channel may have a first portion for positioning the rod. The channel may have a second portion for advancing the rod, such that rotating the collar advances the rod in the channel.

U.S. Published Patent Application No. 2009/0005813 A1 describes a polyaxial screw device and system for spinal fixation and dynamic stabilization. The reference describes hinged connections, cam-style mechanisms, and planar connectors to enable surgeons to attach to an implanted bone fastener or connect to an elongated member from a lateral approach.

FR 2,706,762 A1 describes a screw for a vertebral guide rod that comprises a head and a threaded section. The head comprises a first transverse channel, a guide-rod introduction slot emerging axially in the first channel, and a second transverse channel secant to the first channel. The first and second channels have cross-sections similar to that of the guide rod. A tapped bore emerging in the second channel receives a set screw.

U.S. Pat. No. 7,766,946 B2 describes a device for securing a spinal rod to a fixation device, such as a pedicle screw or a lamina hook. The device includes a head portion configured to receive a spinal rod, a locking cap configured to engage the head portion and the spinal rod upon rotation of the locking cap relative to the head portion to secure the position of the head portion and the locking cap relative to the spinal rod, and a fastener portion extending from the head portion and configured to engage the spine.

U.S. Pat. No. 9,333,017 B2 describes a polyaxial bone anchoring device. The device includes a bone anchoring element having a shank and a head, a head receiving part having a first end, an open second end, and a hollow interior portion for receiving the head therein, a locking ring configured to be mounted around the head receiving part and having a rod receiving portion, a cap configured to be connected to the head receiving part, the cap having a central axis and two opposite legs extending in a direction of the central axis, and a locking element configured to extend from the cap to lock relative positions of the bone anchoring element and an inserted rod relative to the head receiving part. The cap is rotatable relative to the head receiving part between a first position, in which the cap is movable and a second position, in which the legs engage the head receiving part.

U.S. Pat. No. 8,672,972 B2 describes a skeletal stabilization system. The system includes a base, a longitudinal member, and a retaining member. The base includes an engagement surface with a surface area that is positioned in contact with a bone to atraumatically or traumatically engage the base to the bone. The retaining member engages the base to retain the longitudinal member relative to the base so that the longitudinal member can provide a desired stabilization effect to one or more adjacent bony portions.

U.S. Pat. No. 8,048,124 B2 describes a bone screw assembly. The assembly includes a tulip-shaped seat, a bone fixation device, a ring-shaped washer, a rod, and a cap. The tulip-shaped seat comprises a through opening dimensioned to receive the bone fixation device and a horizontal channel dimensioned to receive the rod. The washer is placed into the seat on top of the bone fixation device head and comprises first and second side tabs and a first pair of upward extending projections separated by a first gap and a second pair of upward extending projections separated by a second gap. The side tabs interface with a groove formed in the bottom portion of the seat. The rod is placed within the channel and positioned within a groove formed on the top surface of the washer. The cap includes first and second projections extending downward from its bottom surface and each of the first and second downward projections comprises first and second sidewise extending ridges. The first ridges of the first and second projections are aligned and placed within the first and second gaps of the washer, respectively, and interface with a first groove formed on the side portion of the seat and the second ridges interface with a second groove on the side portion of the seat when the cap is rotate.

U.S. Pat. No. 9,655,650 B2 describes a bone attachment device. The device comprises an attachment collar having a hinged lid and may also comprise a bone fastener (such as a bone screw). The device may be used together with a spinal stabilization rod and one or more additional bone attachment devices.

Various references describe attempts at remedying the factors contributing to the difficulties associated with typical spinal fusion devices or assemblies, such as pedicle screw assemblies. Thus, a need exists for a pedicle screw system that substantially reduces and/or prevents relative motion between spinal segments that are being fused. In particular, a need exists for a pedicle screw system that provides an integrated locking mechanism to secure the pedicle screw system into a spinal segment region. Multiple embodiments of this invention are presented in the drawings and will be described in more detail herein.

SUMMARY OF THE EMBODIMENTS

The present invention and its embodiments relate to a pedicle screw system that comprises a pedicle screw and a tulip assembly with an integrated locking mechanism. In particular, the present invention and its embodiments provide a pedicle screw system that substantially reduces and/or prevents relative motion between spinal segments that are being fused and also provides an integrated locking mechanism to secure the pedicle screw system into a spinal segment region.

In a first example, a pedicle screw system is described. The pedicle screw system includes a body portion affixed to a substantially spherical head portion. The body portion is located at a distal end and the substantially spherical head portion is located at a proximal end of the pedicle screw. The body portion comprises threads configured to penetrate and secure the pedicle screw system within a spinal segment region. Moreover, the body portion may include one or more fenestrations located between the threads. Further, the distal end of the body portion of the pedicle screw is cannulated.

The proximal end of the substantially spherical head portion of the pedicle screw comprises driving features. A driving tool, such as a screw driver, is configured to engage the driving features of the substantially spherical head portion of the pedicle screw to place and secure the pedicle screw system into a spinal segment region. In examples, the spinal segment region includes pedicles of a L4-L5 spinal segment region. However, it should be appreciated that the spinal segment region is not limited to this region explicitly listed herein.

The pedicle screw system also includes a tulip assembly. The tulip assembly comprises a tulip ring and a tulip body. The tulip ring has a proximal end disposed opposite a distal end. The proximal end of the tulip ring includes: an access opening, a first incline plane disposed on a surface of the tulip ring on a first side, and a second incline plane disposed on the surface of the tulip ring on a second side. The first side is disposed opposite the second side. The distal end of the tulip ring includes: a thru bore located in a center of the tulip ring, a first pin located on an interior of the first side, and a second pin located on an interior the second side. The thru bore comprises an inner wall configured to receive and secure a portion of the substantially spherical head portion of the pedicle screw therethrough.

The tulip body has a proximal end disposed opposite a distal end. The proximal end of the tulip body includes a receiving chamber. The distal end of the tulip body includes a first ramp down portion located between a first reduction channel and a first securement portion on the first side. The distal end of the tulip body also includes a second ramp down portion located between a second reduction channel and a second securement portion on the second side. The first side is disposed opposite the second side. The first and the second reduction channels are located in a first plane, the first and the second ramp down portions are located in a second plane, and the first and the second securement portion are substantially spherical in shape and are located in a third plane. The second plane is located between the first and the third plane. The third plane is located distally from the first plane.

Upon rotation of the tulip assembly to an open position, the receiving chamber of the tulip body and the access opening of the tulip ring align such that the receiving chamber and the access opening receive a coupling saddle and a cylindrical rod and the first and the second reduction channels receive the first and the second pin, respectively. The coupling saddle is cylindrical in shape and has a proximal end disposed opposite a distal end. The coupling saddle includes: a main body defining a rod receiving channel for receiving the cylindrical rod, one or more extensions proximally protruding from the main body, and an inner bore formed on the distal end of the main body for coupling the substantially spherical head portion of the pedicle screw. The cylindrical rod is a straight rod comprising a single diameter.

Upon imparting an axial downward force on the cylindrical rod when the tulip assembly is in the open position, the coupling saddle is pushed against the substantially spherical head portion of the pedicle screw to secure the tulip body at an angle relative to the pedicle screw. Moreover, upon imparting the axial downward force on the cylindrical rod when the tulip assembly is in the open position and rotating the tulip assembly to a closed position, the cylindrical rod contacts a sidewall of the tulip body and the first and the second incline plane impart a downward force on the cylindrical rod such that: the cylindrical rod is secured within the tulip body and the tulip assembly is secured at an angle relative to the pedicle screw. Moreover, responsive to this force and rotation of the tulip assembly, the first pin passes the first ramp down portion such that a final portion of the first securement portion captures and secures the first pin in a final locked position and the second pin passes the second ramp down portion such that a final portion of the second securement portion captures and secures the second pin in a final locked position.

In a second example, a tulip assembly configured for use in a pedicle screw system is described. In some examples, the pedicle screw system comprises a stainless-steel material, a titanium material, an alloy material, a chrome material, and/or a cobalt material, among other materials not explicitly listed herein. In some examples, the titanium material is a titanium alloy material. Specifically, the titanium alloy material may be a Ti-6Al-4V alloy material. In other examples, the pedicle screw system is approximately 4.6 mm to approximately 8.5 mm in diameter. In further examples, the pedicle screw system is approximately 6.5 mm in diameter. However, it should be appreciated that various materials comprising the pedicle screw system and various dimensions of the pedicle screw system are contemplated and are not limited to those explicitly listed herein.

The tulip assembly of the second embodiment includes a tulip ring and a tulip body. The tulip ring has a proximal end disposed opposite a distal end. The proximal end of the tulip ring includes: an access opening, a first incline plane disposed on a surface of the tulip ring on a first side, and a second incline plane disposed on the surface of the tulip ring on a second side. The first side is disposed opposite the second side. The first incline plane and the second incline plane decrease in incline towards the distal end of the tulip ring. The distal end of the tulip ring includes: a thru bore located in a center of the tulip ring, a first pin located on an interior of the first side, and a second pin located on an interior the second side.

The tulip body has a proximal end disposed opposite a distal end. The proximal end of the tulip body includes a receiving chamber. The distal end of the tulip body includes a first ramp down portion located between a first reduction channel and a first securement portion on the first side. The distal end of the tulip body also includes a second ramp down portion located between a second reduction channel and a second securement portion on the second side. The first side is disposed opposite the second side. The first and the second reduction channels are located in a first plane, the first and the second ramp down portions are located in a second plane, and the first and the second securement portion are substantially spherical in shape and are located in a third plane. The second plane is located between the first and the third plane. The third plane is located distally from the first plane.

Upon rotation of the tulip assembly to an open position, the receiving chamber of the tulip body and the access opening of the tulip ring align such that the receiving chamber and the access opening receive a coupling saddle and a cylindrical rod and the first and the second reduction channels receive the first and the second pin, respectively. In some examples, the cylindrical rod is a curved rod comprising two or more diameters. In other examples, the cylindrical rod is a straight rod comprising a single diameter.

In a third example, a tulip assembly configured for use in a pedicle screw system is described. The tulip assembly includes a tulip ring and a tulip body. The tulip ring has a proximal end disposed opposite a distal end. The proximal end of the tulip ring includes: an access opening, a first incline plane disposed on a surface of the tulip ring on a first side, and a second incline plane disposed on the surface of the tulip ring on a second side. The first side is disposed opposite the second side. Moreover, the first incline plane and the second incline plane decrease in incline towards the distal end of the tulip ring. The distal end of the tulip ring includes: a thru bore located in a center of the tulip ring, a first pin located on the first side, and a second pin located on the second side.

The tulip body has a proximal end disposed opposite a distal end. The proximal end of the tulip body includes a receiving chamber. The distal end of the tulip body includes a first ramp down portion located between a first reduction channel and a first securement portion on the first side. The distal end of the tulip body also includes a second ramp down portion located between a second reduction channel and a second securement portion on the second side. The first side is disposed opposite the second side. The first and the second reduction channels are located in a first plane, the first and the second ramp down portions are located in a second plane, and the first and the second securement portion are substantially spherical in shape and are located in a third plane. The second plane is located between the first and the third plane. The third plane is located distally from the first plane.

Upon rotation of the tulip assembly to an open position, the receiving chamber of the tulip body and the access opening of the tulip ring align such that the receiving chamber and the access opening receive a coupling saddle and a cylindrical rod and the first and the second reduction channels receive the first and the second pin, respectively.

A fourth example of a pedicle screw system is also described herein. The fourth example of the pedicle screw system includes a pedicle screw, a wave spring, a coupling saddle, a cylindrical rod, and a tulip assembly. The pedicle screw includes a body portion located at a distal end and affixed to a substantially spherical head portion located at a proximal end of the pedicle screw. The body portion comprises threads configured to penetrate and secure the pedicle screw system within a spinal segment region. Moreover, the body portion of the pedicle screw is movable outward from a center of the pedicle screw at an angle up to 30 degrees. In some examples, the wave spring has a thickness of approximately 0.009 mm.

Further, the coupling saddle is cylindrical in shape. The coupling saddle includes a body portion and a first end disposed opposite a second end. A width of the second end is threaded to better couple the cylindrical rod. Further, the body portion includes a rod receiving channel, a first extension member extending from a first location on the first end, and a second extension member extending from a second location on the first end, where the first location is disposed opposite the second location.

The body portion of the coupling saddle also includes a first recess formed between the first extension member and the second extension member at a third location. A first elliptical portion is located at the first recess and extends towards the first end. A second recess is formed between the first extension member and the second extension member at a fourth location. A second elliptical portion is located at the second recess and extends towards the first end. An opening is located proximate the second end. The third location is disposed opposite the fourth location. Additionally, each of the third location and the fourth location are located between the first location and the second location.

The tulip assembly includes a tulip ring and a tulip body. The tulip ring has a proximal end disposed opposite a distal end. The proximal end of the tulip ring includes an access opening, a first incline plane disposed on a surface of the tulip ring on a first side, and a second incline plane disposed on the surface of the tulip ring on a second side. The first side is disposed opposite the second side. The distal end of the tulip ring includes a thru bore located in a center of the tulip ring, a first pin located on an interior of the first side, and a second pin located on an interior the second side.

The tulip body includes a body portion and a proximal end disposed opposite a distal end, where the distal end includes a protrusion section. The body portion includes a first portion extending away from the distal end at a first location. The first portion includes a first ramp down portion located between a first reduction channel and a first securement portion and a first threaded section located in an interior of the first portion proximate the proximal end. The body portion also includes a second portion extending away from the distal end at a second location. The second portion includes a second ramp down portion located between a second reduction channel and a second securement portion and a second threaded section located in an interior of the second portion proximate the proximal end. The first location is disposed opposite the second location.

The body portion also includes a first sloped recess affixed to a first elliptical portion at a third location and a second sloped recess affixed to a second elliptical portion at a fourth location. The third location is disposed opposite the fourth location. Further, each of the third location and the fourth location are located between the first location and the second location. Upon rotation of the tulip assembly to an open position, the receiving chamber of the tulip body and the access opening of the tulip ring align such that the receiving chamber and the access opening receive a coupling saddle and a cylindrical rod and the first and the second reduction channel receive the first and the second pin, respectively.

A fifth example of the pedicle screw system is described herein. In this fifth example, the tulip ring has a proximal end disposed opposite a distal end. The tulip ring, at the proximal end, includes an access opening, a first plane disposed on a surface of the tulip ring on the first side, and a second plane disposed on a surface of the tulip ring on the second side, where the first side is disposed opposite the second side. Threads may be located on an interior of the first plane and on an interior of the second plane. In some examples, the threads are tapered threads. The distal end of the tulip ring is not threaded, but includes a circular ring having a thru bore disposed therein.

The tulip body of the fifth example includes the proximal end disposed opposite the distal end. On the distal end, the tulip body includes a protrusion section that may be semicircular in shape. The proximal end includes a body portion. The body portion includes a first portion extending away from the distal end of the tulip body at a first location and a second portion extending away from the distal end of the tulip body at a second location. The first location is disposed opposite the second location. A first recess is located between the first portion and the second portion at a third location. A second recess is located between the first portion and the second portion at a fourth location. Each of the first recess and the second recess are U-shaped. It should be appreciated that the shape of each of the first recess and the second recess are not limited to such. The third location is disposed opposite the fourth location. Moreover, each of the third location and the fourth location are disposed between the first location and the second location.

Moreover, the first portion of the tulip body near the distal end comprises the first ramp down portion located between the first reduction channel and the first securement portion. The second portion of the tulip body near the distal end comprises the second ramp down portion located between the second reduction channel and the second securement portion.

Further, an exterior of each of the first portion and the second portion near the proximal end of the tulip body comprise a threaded section. An interior of each of the first portion and the second portion near the proximal end of the tulip body comprise another threaded section. Additionally, the interior threads of the tulip ring engage the exterior threaded section of the tulip body in an interlocking manner such that the threads cannot be pulled apart from one another. Such eliminates splay and increases the axial preload retained by the pedicle screw in the final locked position.

In general, the present invention succeeds in conferring the following benefits and objectives.

It is an object of the present invention to provide a pedicle screw assembly that substantially reduces and/or prevents relative motion between spinal segments that are being fused.

It is an object of the present invention to provide a pedicle screw assembly that provides an integrated locking mechanism to secure the pedicle screw system into a spinal segment region.

It is an object of the present invention to provide a pedicle screw assembly that provides an integrated locking mechanism to prevent slippage of the pedicle screw system when implanted in the spinal segment region.

BRIEF DESCRIPTION OF THE DRAWINGS

FIG. 2A and FIG. 2B depict perspective views of a first embodiment of a pedicle screw system having a tulip assembly in an open position, according to at least some embodiments described herein.

DESCRIPTION OF THE PREFERRED EMBODIMENTS

Figure 1A:
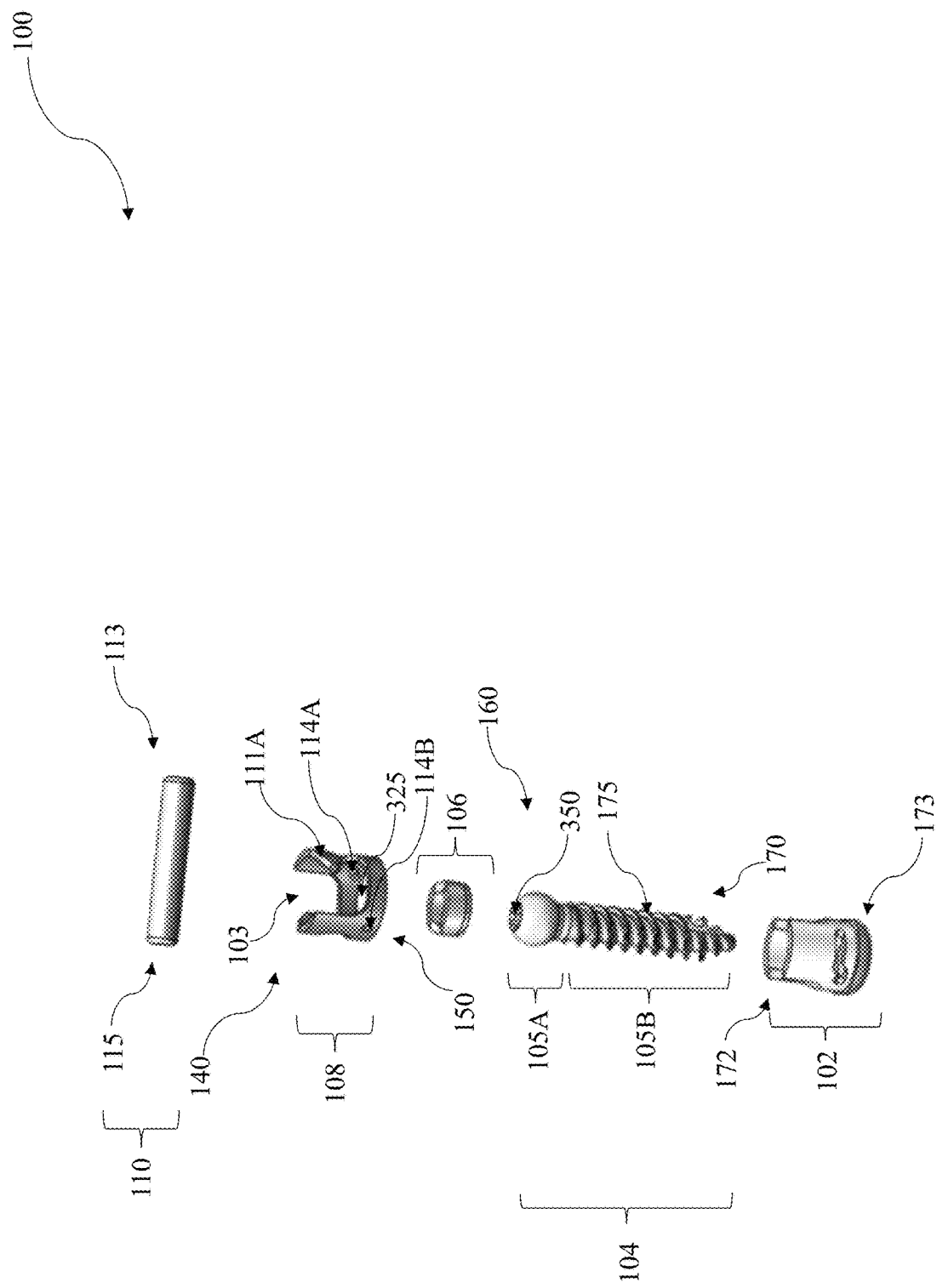
FIG. 1A depicts an exploded view of a first embodiment of a pedicle screw system comprising a pedicle screw, a tulip ring, and a tulip body according to at least some embodiments described herein.

The preferred embodiments of the present invention will now be described with reference to the drawings. Identical elements in the various figures are identified with the same reference numerals.

Reference will now be made in detail to each embodiment of the present invention. Such embodiments are provided by way of explanation of the present invention, which is not intended to be limited thereto. In fact, those of ordinary skill in the art may appreciate upon reading the present specification and viewing the present drawings that various modifications and variations can be made thereto.

Figure 1B:
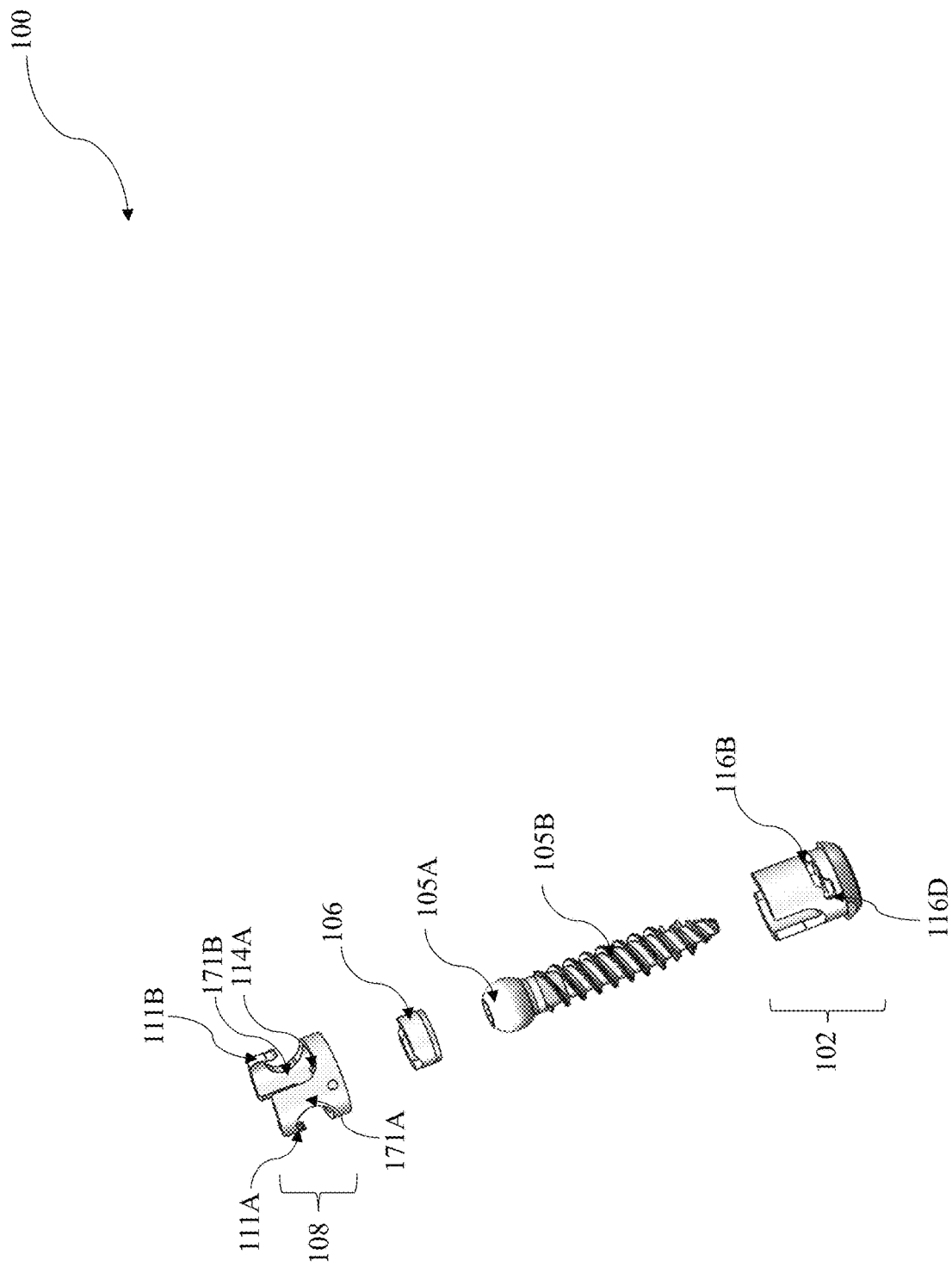
FIG. 1B depicts an exploded view of a first embodiment of a pedicle screw system comprising a pedicle screw and a tulip assembly comprising a tulip ring and a tulip body, according to at least some embodiments described herein.

According to FIG. 1A and FIG. 1B, exploded views of a first embodiment of a pedicle screw system 100 are depicted. According to some examples, the first embodiment of the pedicle screw system 100 may be used for fixation of spinal segments (e.g., in a spinal fusion surgery) and may be useful when minimally invasive surgery (MIS) techniques are employed.

As depicted in FIG. 1A and FIG. 1B, the first embodiment of the pedicle screw system 100 may comprise a pedicle screw 104 and a tulip assembly. The tulip assembly may include a tulip ring 108 and a tulip body 102. The first embodiment of the pedicle screw system 100 may be approximately 4.6 mm to approximately 8.5 mm in diameter. In further examples, the first embodiment of the pedicle screw system 100 is approximately 6.5 mm in diameter.

It should be appreciated that the first embodiment of the pedicle screw system 100 may comprise one or more materials, such as a stainless-steel material, a cobalt material, a titanium material, an alloy material, and/or a cobalt material, among other materials not explicitly listed herein. In examples, the first embodiment of the pedicle screw system 100 may comprise a titanium alloy material. In specific examples, the titanium alloy material may be a Ti-6Al-4V alloy material. In other examples, the first embodiment of the pedicle screw system 100 may comprise a cobalt chrome material. It should be appreciated that the dimensions of the first embodiment of the pedicle screw system 100 and the materials listed comprising the first embodiment of the pedicle screw system 100 are non-limiting and other dimensions and/or materials are contemplated herein. Moreover, it should be appreciated that the pedicle screw 104 described herein may be any pedicle screw used in the instant technical field.

As an illustrative example, the pedicle screw 104 may comprise a substantially spherical head portion 105A at a proximal end 160 that may be affixed to a body portion 105B located at a distal end 170. The body portion 105B may comprise threads 175 that may penetrate and secure the first embodiment of the pedicle screw system 100 into a bone of a patient at a desired location. In an example, the threads 175 may penetrate and secure the first embodiment of the pedicle screw system 100 into a spinal system of a patient. In an example, the spinal system may be a spinal segment region 200. In other examples, the spinal segment region 200 includes pedicles of a L4-L5 spinal segment region. In other examples, multiple pedicle screw systems 100 may be secured into the bone or the spinal segment region 200 of the patient, where a placement and/or a quantity of first embodiment of the pedicle screw system 100 may be pre-operatively determined based on a pre-operative examination of the patient's spinal system. In further examples, the tulip assembly may comprise a cobalt-chrome material and the body portion 105B may comprise a titanium material. It should be appreciated that the materials listed comprising the pedicle screw system 100 are non-limiting and other materials are contemplated herein.

Figure 1C:
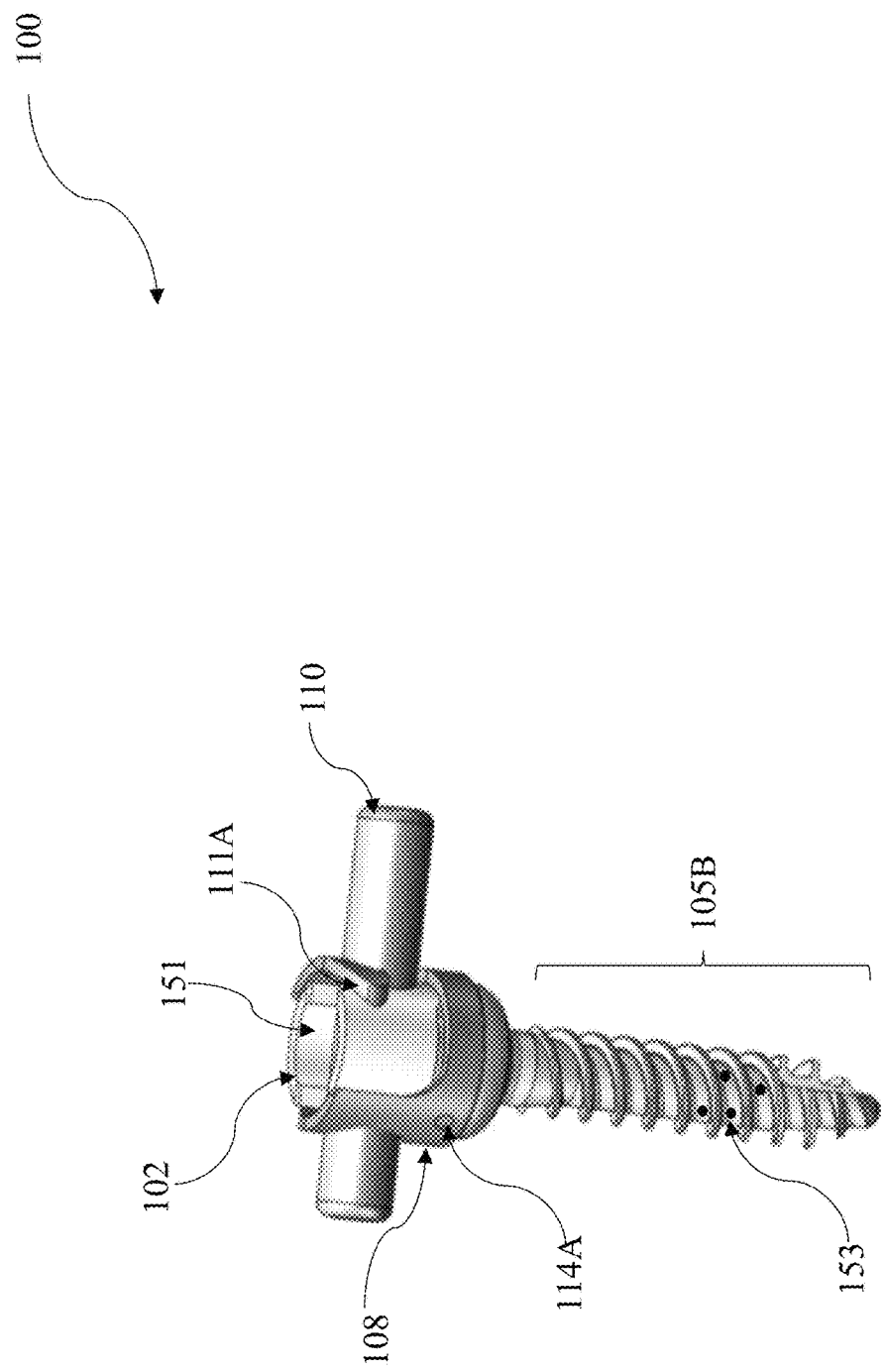
FIG. 1C depicts a perspective view of a first embodiment of an assembled pedicle screw system, according to at least some embodiments described herein.

In additional examples, the body portion 105B of the pedicle screw 104 may contain one or more fenestrations 153 (as shown in FIG. 1C) located between the threads 175. It should be appreciated that the one or more fenestrations 153 may provide a reduction in post-operative slip degree of the pedicle screw 104.

Moreover, the distal end 170 of the body portion 105B of the pedicle screw 104 may be cannulated. According to examples, the proximal end 160 of the substantially spherical head portion 105A may comprise driving features 350 that may be engaged by a driving tool 180 (of FIG. 27 and FIG. 28) to secure the first embodiment of the pedicle screw system 100 into the spinal segment region 200 (as shown in FIG. 29A, FIG. 29B, FIG. 29C, FIG. 29D, and FIG. 29E). Examples of the driving tool 180 include: a screw driver, a counter-torque tool, a turning cap tool, and/or an axial rod persuader tool. It should be appreciated that the driving tool 180 may be any tool that attaches to the tulip assembly and other tools not explicitly listed herein are contemplated.

As shown in FIG. 1A, the tulip ring 108 of the first embodiment of the pedicle screw system 100 may comprise a proximal end 140 disposed opposite a distal end 150. The distal end 150 of the tulip assembly may be configured to receive and secure the substantially spherical head portion 105A of the pedicle screw 104 to the tulip assembly. The proximal end 140 of the tulip ring 108 may comprise an access opening 103, a first incline plane 111A (as shown in FIG. 1A and FIG. 1B) disposed on a surface of the tulip ring 108 on a first side 171A (as shown in FIG. 1B), and a second incline plane 111B (as shown in FIG. 1B) disposed on a surface of the tulip ring 108 on a second side 171B (as shown in FIG. 1B). The first side 171A is disposed opposite the second side 171B. In some examples, the first incline plane 111A and the second incline plane 111B decrease in incline towards the distal end 150 of the tulip ring 108.

The distal end 150 of the tulip ring 108 may be configured to receive and secure the substantially spherical head portion 105A of the pedicle screw 104 near the proximal end 160 of the pedicle screw 104. The distal end 150 of the tulip ring 108 may comprise a thru bore 325 (of FIG. 1A) located in a center of the tulip ring 108, a first pin 114A (of FIG. 1A and FIG. 1B) located on an interior of the first side 171A (of FIG. 1B), and a second pin 114B (of FIG. 1A) located on an interior of the second side 171B (of FIG. 1B). The first side 171A is disposed opposite the second side 171B, as shown in FIG. 1B.

The thru bore 325 may be configured to receive a portion of the substantially spherical head portion 105A of the pedicle screw 104 therethrough. Further, the thru bore 325 may comprise an inner wall that may secure the substantially spherical head portion 105A of the pedicle screw 104. Moreover, an internal diameter of the thru bore 325 is consistent such that a frictional fit may be maintained with the substantially spherical head portion 105A of the pedicle screw 104. In some examples, the tulip ring 108 may be pre-assembled. In other examples, the tulip ring 108 may not be pre-assembled.

The tulip body 102 of the first embodiment of the pedicle screw system 100 may comprise a proximal end 172 disposed opposite a distal end 173, as shown in FIG. 1A. The proximal end 172 of the tulip body 102 may comprise a receiving chamber 151 (as shown in FIG. 1C). The distal end 173 of the tulip body 102 may comprise: a first ramp down portion 116E (as shown in FIG. 4) located between a first reduction channel 116A (as shown in FIG. 4) and a first securement portion 116C (as shown in FIG. 4) on a first side of the tulip body 102 and a second ramp down portion (not shown) located between a second reduction channel 116B (as shown in FIG. 1B) and a second securement portion 116D (as shown in FIG. 1B) on a second side of the tulip body 102.

Figure 4:
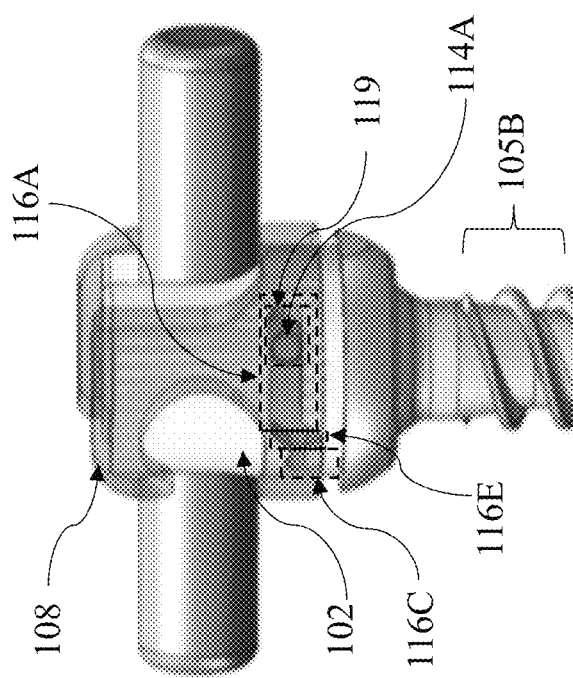
FIG. 4 depicts a perspective view of initial rotation of a tulip assembly after a first embodiment of the pedicle screw system receives a cylindrical rod, according to at least some embodiments described herein.

According to examples, the first reduction channel 116A (as shown in FIG. 4) and the second reduction channel 116B (as shown in FIG. 1B) are located in a first plane. The first ramp down portion 116E (as shown in FIG. 4) and the second ramp down portion (not shown) are located in a second plane. The first securement portion 116C (as shown in FIG. 4) and the second securement portion 116D (as shown in FIG. 1B) are located in a third plane. According to some examples, the second plane is located between the first and the second plane. Moreover, the third plane is located distally from the first plane. Moreover, the first securement portion 116C (as shown in FIG. 4) and the second securement portion 116D (as shown in FIG. 1B) are substantially spherical in shape. In some examples, the first securement portion 116C (as shown in FIG. 4) and the second securement portion 116D (not shown) are spherical in shape.

As depicted in FIG. 1A, a cylindrical rod 110 may comprise a first end 113 disposed opposite a second end 115. In examples, the cylindrical rod 110 is a straight rod comprising a single diameter. In another example, the cylindrical rod 110 is the straight rod comprising two or more diameters. In other examples, the cylindrical rod 110 is a curved or a bent rod comprising a single diameter. In further examples, the cylindrical rod 110 is the curved or the bent rod comprising two or more diameters.

According to some embodiments, the coupling saddle 106 may be placed within the access opening 103 of the tulip ring 108. The access opening 103 is sized to allow the coupling saddle 106 and the cylindrical rod 110 to be placed within the tulip assembly. Specifically, the coupling saddle 106 is cylindrical in shape and comprises a main body defining a rod receiving channel, one or more extensions proximally protruding from the main body, and an inner bore formed on the distal end of the main body for coupling the substantially spherical head portion 105A of the pedicle screw 104.

Figure 2B:
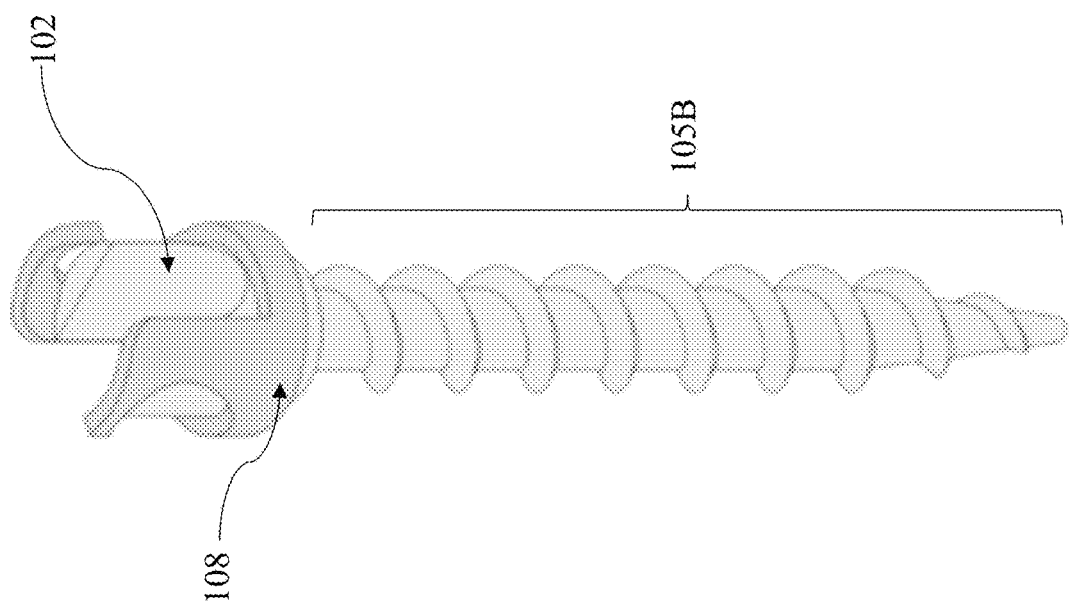
Figure 2C:
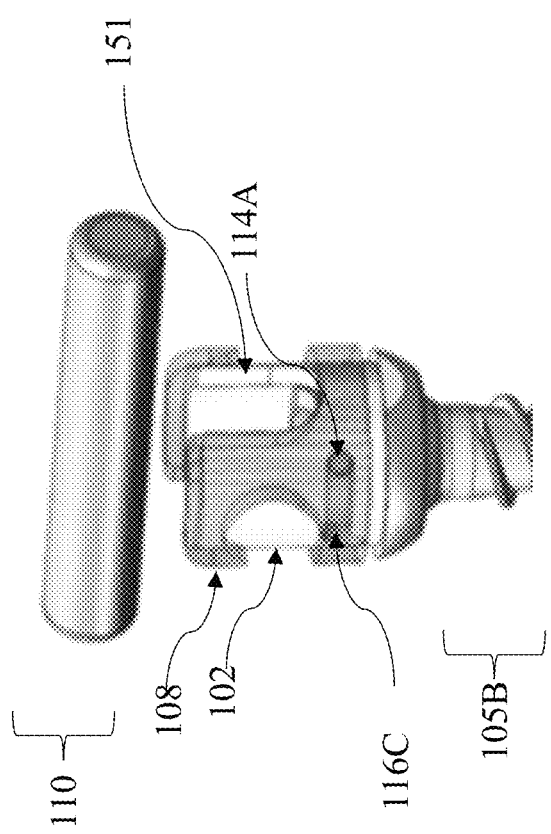
FIG. 2C depicts another perspective view of a first embodiment of a pedicle screw system having a tulip assembly in an open position and being configured to receive a cylindrical rod, according to at least some embodiments described herein.
Figure 3:
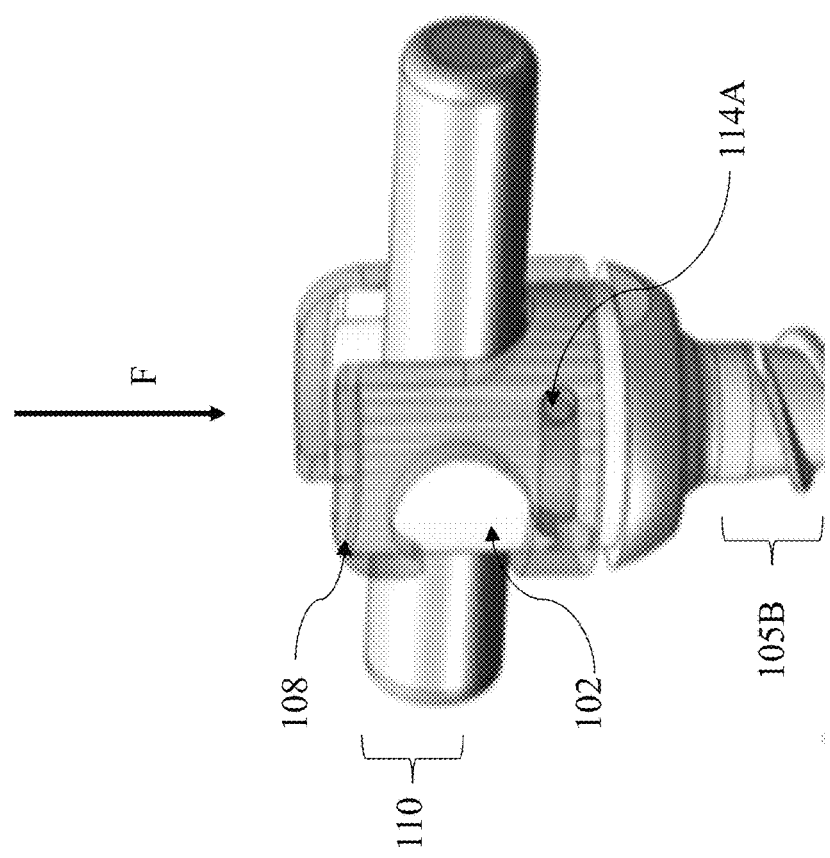
FIG. 3 depicts a perspective view of a first embodiment of a pedicle screw system receiving a cylindrical rod, according to at least some embodiments described herein.

According to some examples, and as depicted in FIG. 2A and FIG. 2B, the tulip assembly may be rotated to the open position. Such rotation in depicted in FIG. 2C. It should be appreciated that the rotation depicted in FIG. 2C is counterclockwise, or CCW, rotation. During such rotation, the first reduction channel 116A (as shown in FIG. 4) receives the first pin 114A (as shown in FIG. 2C, FIG. 3, FIG. 4) and the second reduction channel 116B (as shown in FIG. 1B) receives the second pin 114B (as shown in FIG. 1A). The rotation may occur to a maxim. The rotation to the open position ceases when the first pin 114A is in an extreme position 119 within the first reduction channel 116A (as shown in FIG. 4). The extreme position 119 means that the first pin 114A cannot move further in the first reduction channel 116A (as shown in FIG. 4) and is at a maximum distance from the first securement portion 116C (as shown in FIG. 4). Upon rotation of the tulip assembly to the open position, the receiving chamber 151 of the tulip body 102 and the access opening 103 of the tulip ring 108 align such that the receiving chamber 151 and the access opening 103 receive the coupling saddle 106 and the cylindrical rod 110 therein.

As shown in FIG. 3 by the downward arrow labeled "F," an axial downward force may be imparted or applied on the cylindrical rod 110 when the tulip assembly is in the open position. When such action occurs, the coupling saddle 106 moves within the tulip assembly and is pushed against the substantially spherical head portion 105A of the pedicle screw 104 to secure the pedicle screw 104. It should be appreciated that the size of the cylindrical rod 110 determines how far the coupling saddle 106 is pushed against the substantially spherical head portion 105A of the pedicle screw 104.

Figure 5:
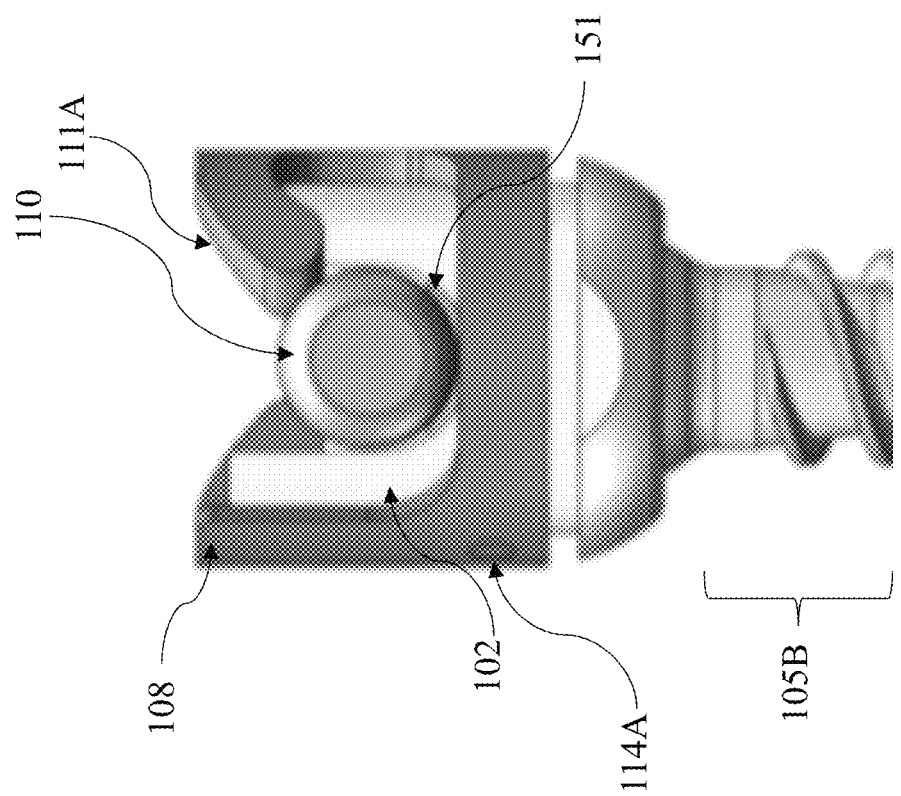
FIG. 5 depicts a perspective view of a first embodiment of a pedicle screw system having a tulip assembly in an intermediate position after receiving a cylindrical rod therein, according to at least some embodiments described herein.
Figure 6:
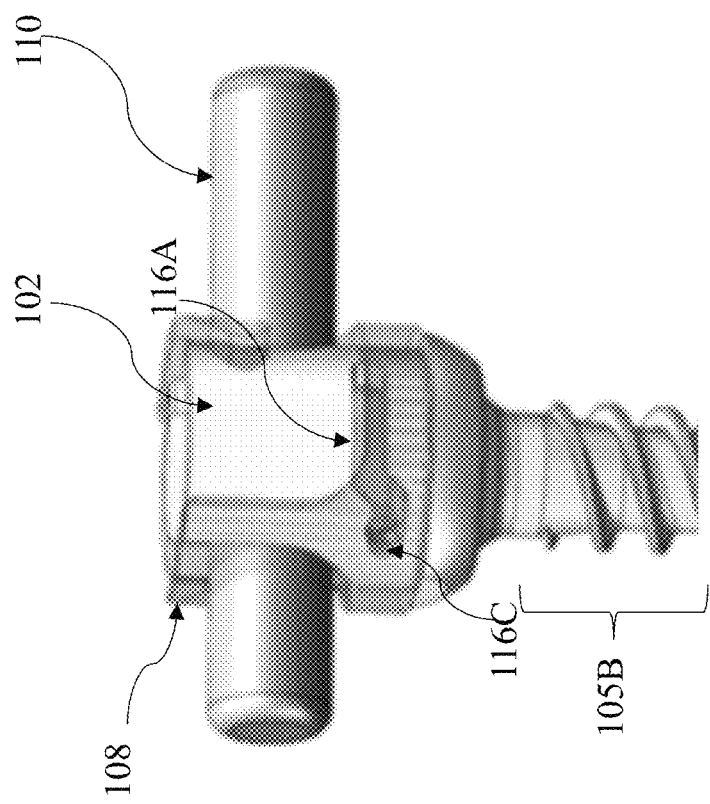
FIG. 6 depicts a perspective view of a first embodiment of a pedicle screw system having a tulip assembly in a closed position after receiving a cylindrical rod therein, according to at least some embodiments described herein.

FIG. 4-FIG. 6 depict a perspective view of rotation of the tulip assembly after the pedicle screw system receives a cylindrical rod. Specifically, FIG. 4 depicts initial rotation of the tulip assembly, FIG. 5 depicts the tulip assembly in an intermediate position, and FIG. 6 depicts the tulip assembly in a closed or a final position.

Figure 8A:
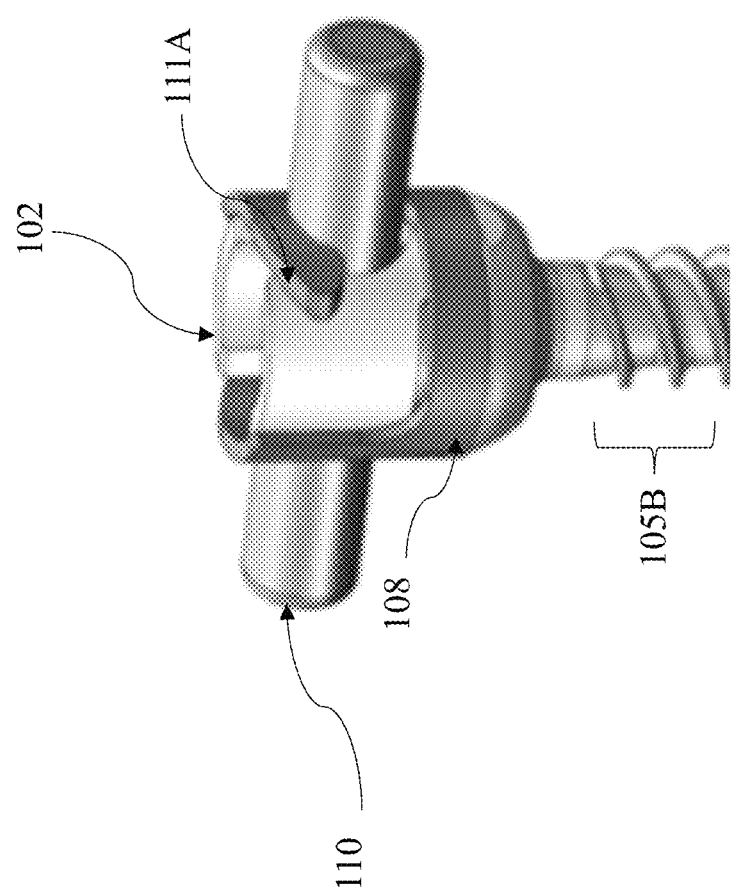
FIG. 8A depicts a perspective view of a first embodiment of a pedicle screw system having a tulip assembly in a closed position after receiving a cylindrical rod therein, according to at least some embodiments described herein.
Figure 9:
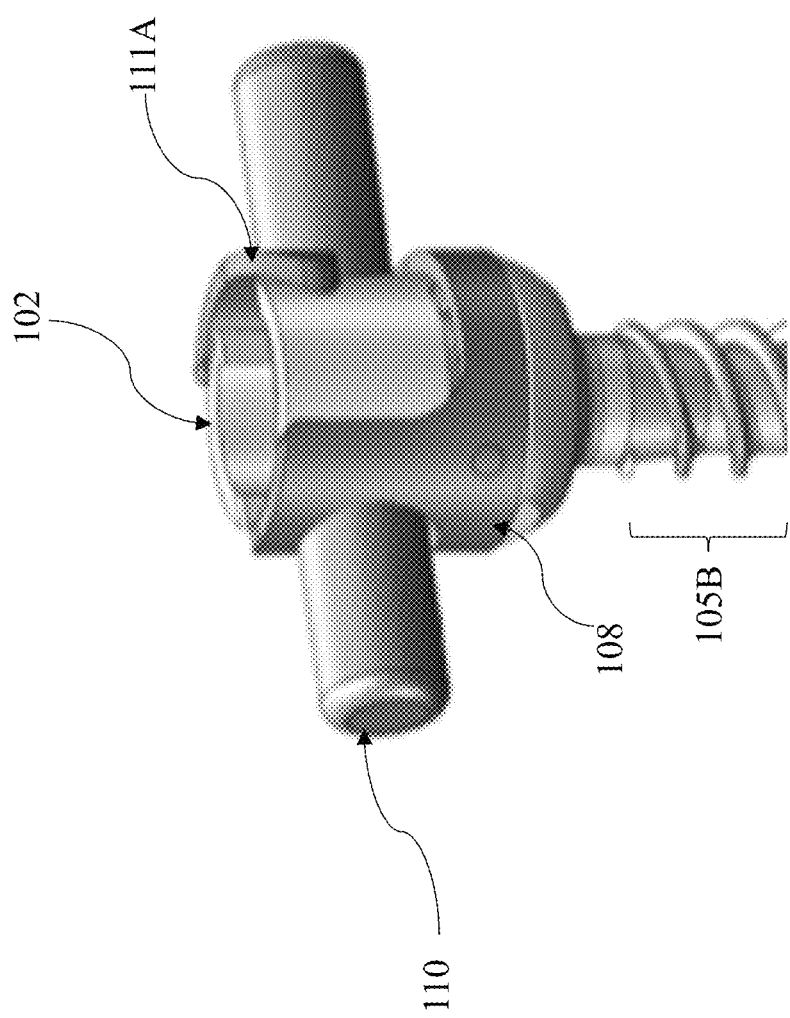
FIG. 9 depicts a perspective view of a first embodiment of a pedicle screw system having a tulip assembly in a closed position after receiving a cylindrical rod therein, according to at least some embodiments described herein.
Figure 10:
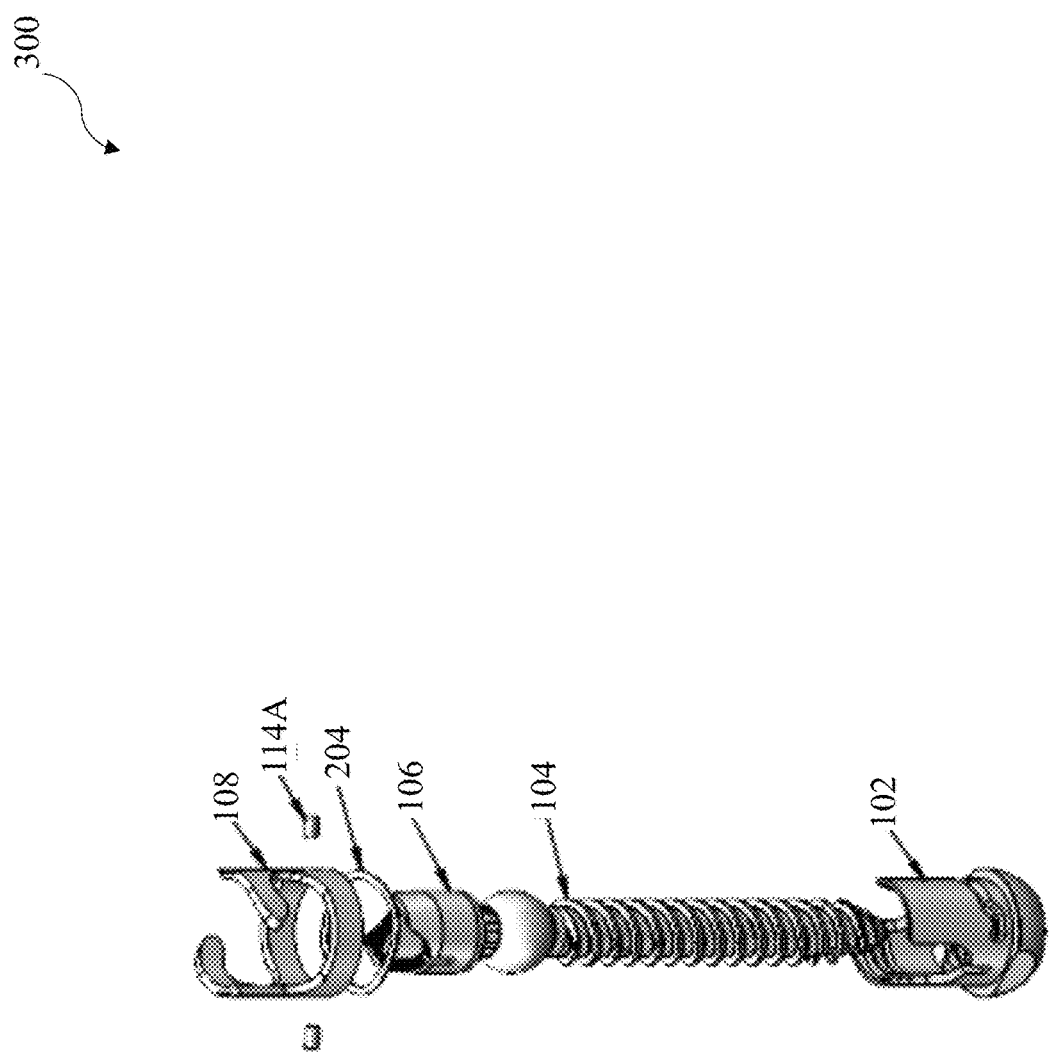
FIG. 10 depicts an exploded view of a second embodiment of a pedicle screw system, according to at least some embodiments described herein.
Figure 11:
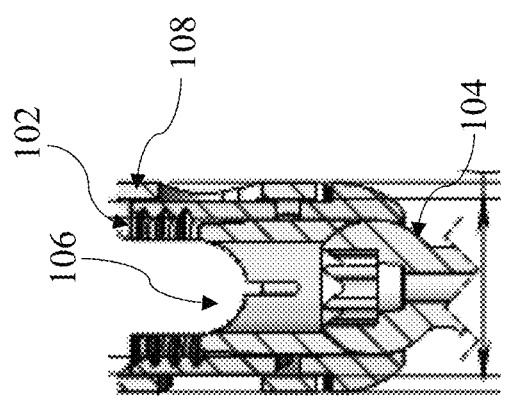
FIG. 11 depicts a perspective view of several components assembled for a second embodiment of a pedicle screw system, according to at least some embodiments described herein.

As shown in FIG. 5 and FIG. 6, upon imparting the axial downward force on the cylindrical rod 110 (as shown in FIG. 3 by the downward arrow labeled "F") when the tulip assembly is in the open position and rotating the tulip assembly to a closed position (as shown in FIG. 8A and FIG. 9), the cylindrical rod 110 is configured to contact a sidewall of the tulip body 102, the first incline plane 111A imparts a downward force on the cylindrical rod 110, and the second incline plane 111B imparts a downward force on the cylindrical rod 110. The downward force that the first incline plane 111A and the second incline plane 111B impart on the cylindrical rod 110 is a retention force on the cylindrical rod 110 that secures the cylindrical rod 110 in place as seated against the coupling saddle 106 within the tulip assembly. Specifically, as a result of the axial downward force exerted on the cylindrical rod 110, an interference fit is created such that the cylindrical rod 110 is secured within the tulip assembly and the tulip assembly is secured at an angle relative to the pedicle screw 104. It should be appreciated that an interference fit is one where, responsive to insertion of one component into another component whose diameter is slightly smaller than the component being inserted, a fit is created between the two components.

Figure 7:
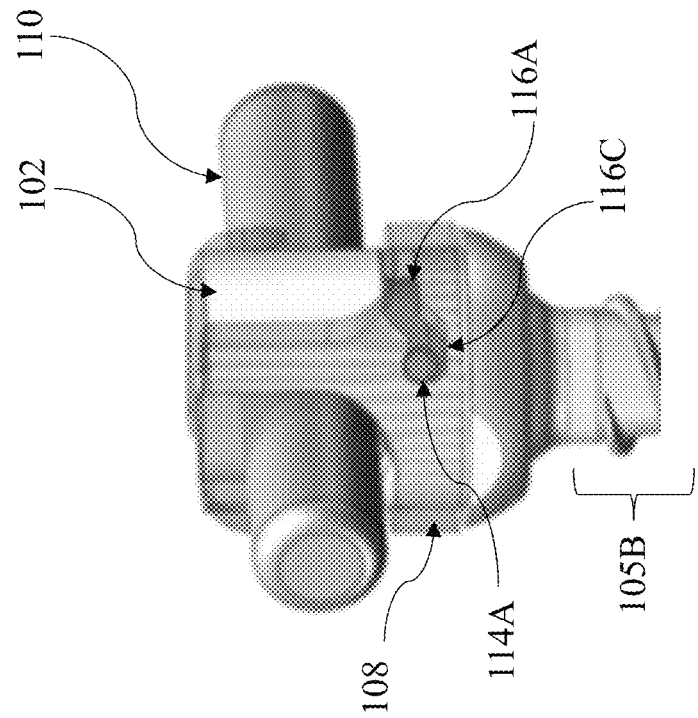
FIG. 7 depicts a perspective view of a first embodiment of a pedicle screw system having a tulip assembly in a closed position such that a first and a second securement channel receive and secure a first and a second pin, respectively, according to at least some embodiments described herein.

Moreover, as a result of the axial downward force exerted on the cylindrical rod 110 when the tulip assembly is in the open position and rotation of the tulip assembly to the closed position, the first pin 114A leaves the first reduction channel 116A and approaches the first ramp down portion 116E (as shown in FIG. 4) and the second pin 114B leaves the second reduction channel 116B and approaches the second ramp down portion (not shown). As an illustrative example, when the first pin 114A approaches the ramp down portion 116E, axial force applies pressure of the cylindrical rod 110. A final portion of the first securement portion 116C (as shown in FIG. 4) is located opposite the extreme position 119. The final portion of the first securement portion 116C captures and secures the first pin 114A (as shown in FIG. 6 and FIG. 7). Moreover, the final portion of the first securement portion 116C (as shown in FIG. 4) prevents the first pin 114A from backing out of this final seated position.

Figure 8B:
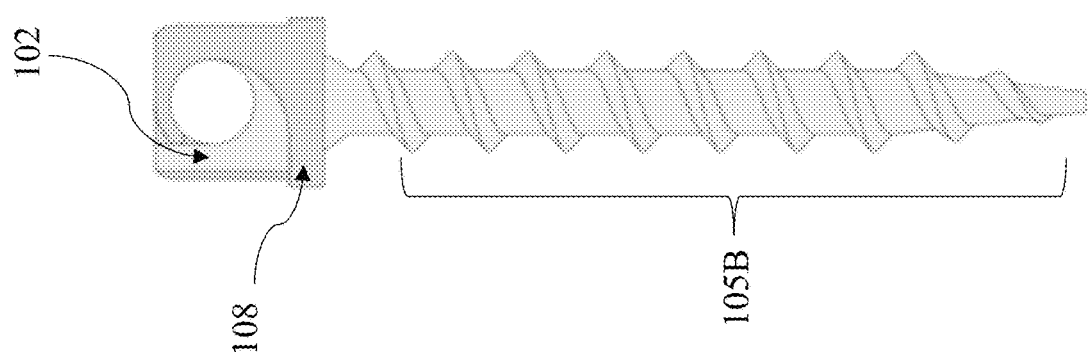
FIG. 8B and FIG. 8C depict perspective views of a first embodiment of a pedicle screw system having a tulip assembly in a closed position, according to at least some embodiments described herein.
Figure 8C:
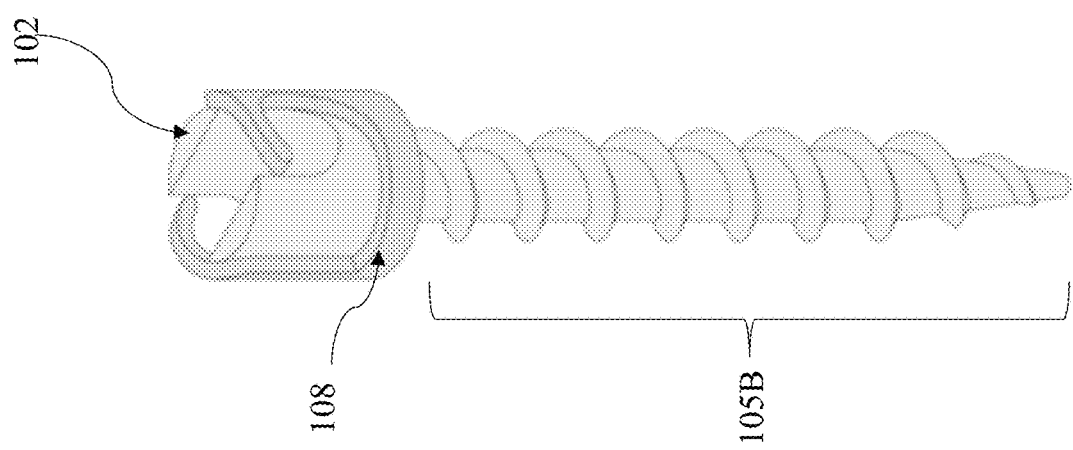

Similarly, when the second pin 114B approaches the second ramp down portion (not shown), axial force applies pressure of the cylindrical rod 110. A final portion (not shown) of the second securement portion 116D (as shown in FIG. 4) captures and secures the second pin 114B. Moreover, the final portion of the second securement portion 116D (as shown in FIG. 4) prevents the second pin 114B from backing out of this final seated position. Further, the securement of the first pin 114A in the first securement portion 116C and the second pin 114B in the second securement portion 116D locks or secures the pedicle screw system 100 in place. For illustrative purposes, the tulip assembly is depicted in FIG. 8B and FIG. 8C in the closed position without the cylindrical rod 110.

Moreover, when the tulip assembly is in the closed or final position, exertion of another axial downward force on the cylindrical rod 110 is required while rotating the tulip assembly CCW to the open position to release or unsecure the cylindrical rod 110 from the tulip assembly.

Figure 27:
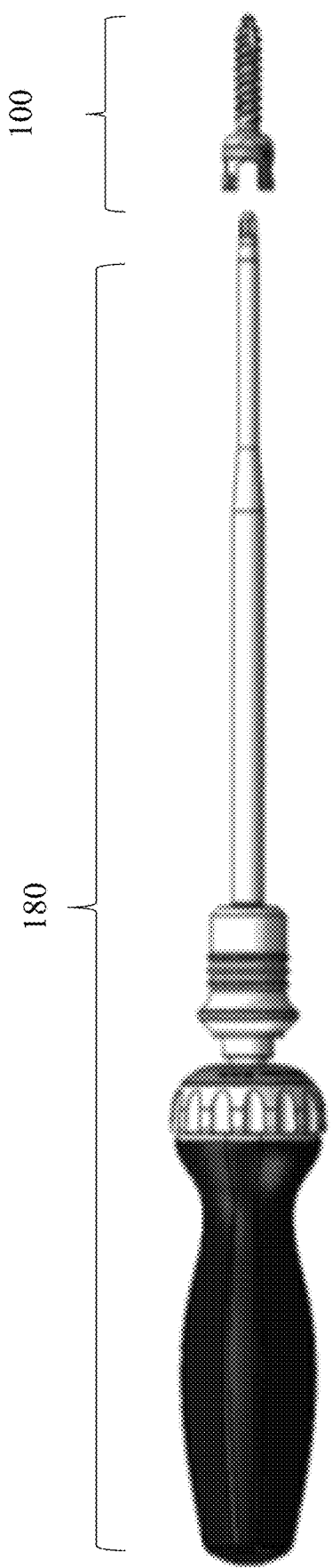
FIG. 27 and FIG. 28 depict perspective views of a driving tool engaging driving features of a substantially spherical head portion of a pedicle screw in a pedicle screw system, according to at least some embodiments described herein.
Figure 28:
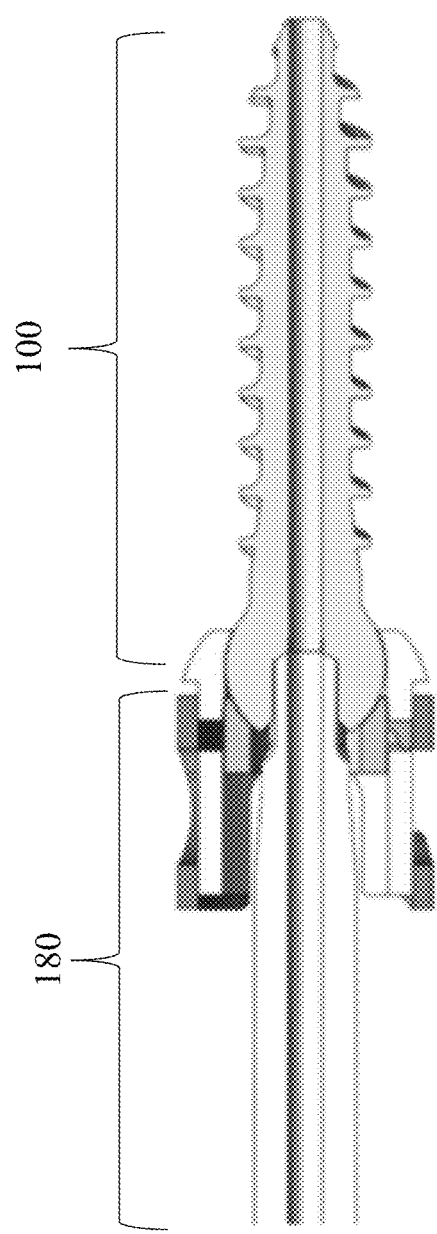

A method to secure the first embodiment of the pedicle screw system 100 into the bone of a patient at a desired location is also contemplated herein and depicted in FIG. 27, FIG. 28, and FIG. 29A-FIG. 29E. As depicted in FIG. 27 and FIG. 28, the proximal end 160 of the substantially spherical head portion 105A may comprise driving features 350 that may be engaged by a driving tool 180 to secure the pedicle screw system 100 into a spinal segment region 200 (as shown in FIG. 29A-FIG. 29E) of the patient. In examples, the driving tool 180 may be a screw driver, among other example devices not explicitly listed herein.

Figure 29A:
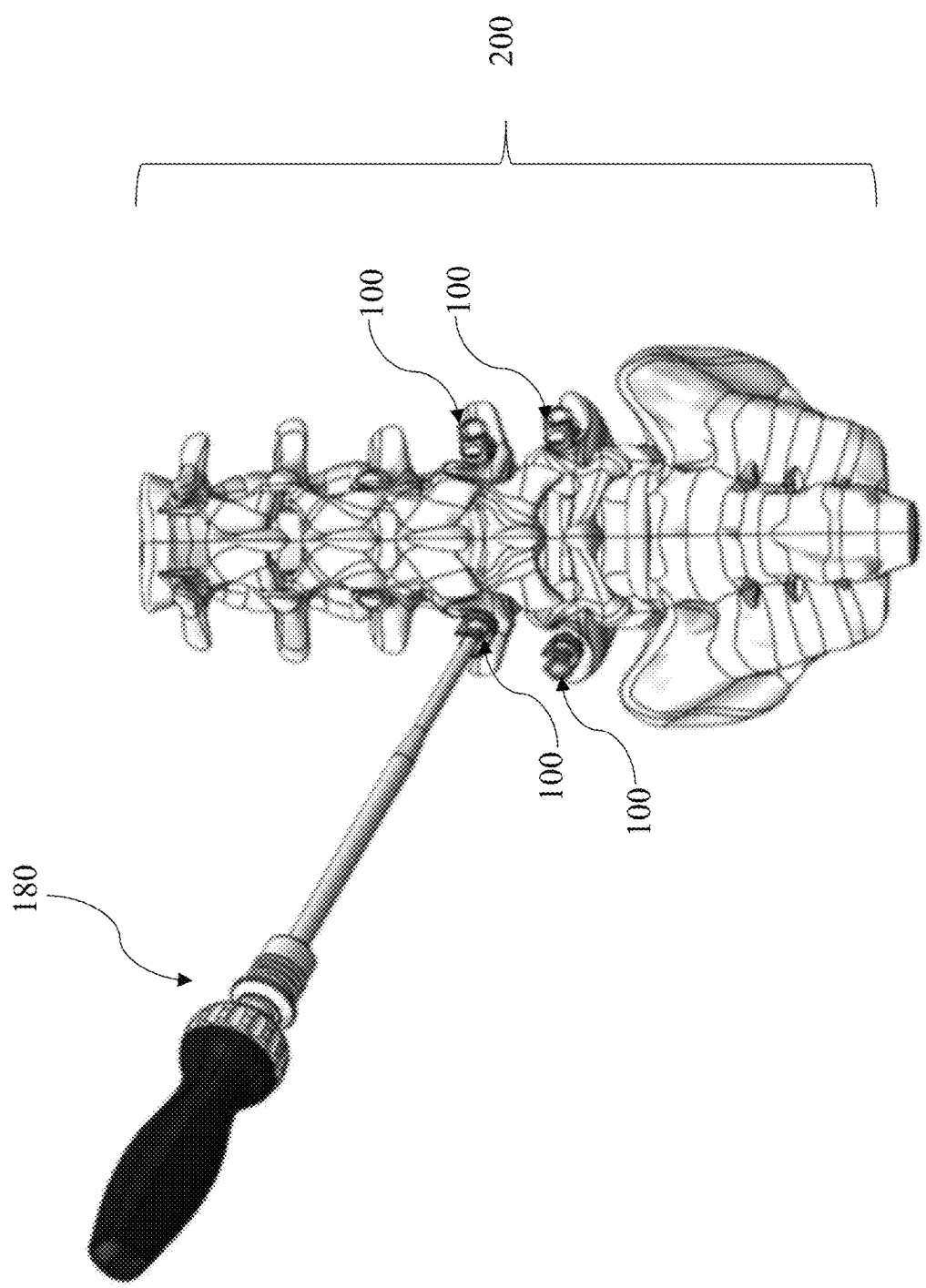
FIG. 29A and FIG. 29B depict perspective views of a driving tool engaging driving features of a substantially spherical head portion of a pedicle screw in a pedicle screw system to place the pedicle screw system into a spinal segment region, according to at least some embodiments described herein.
Figure 29B:
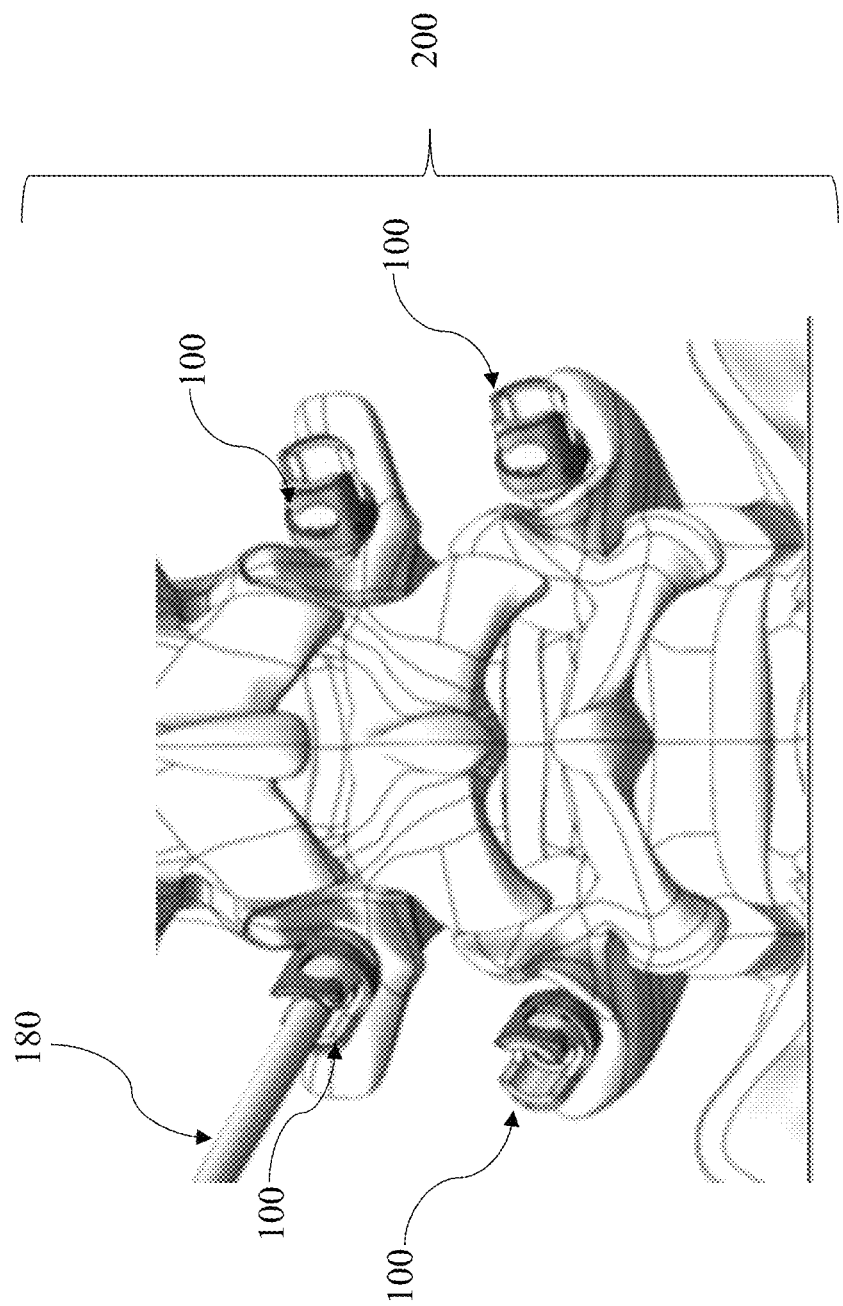
Figure 29C:
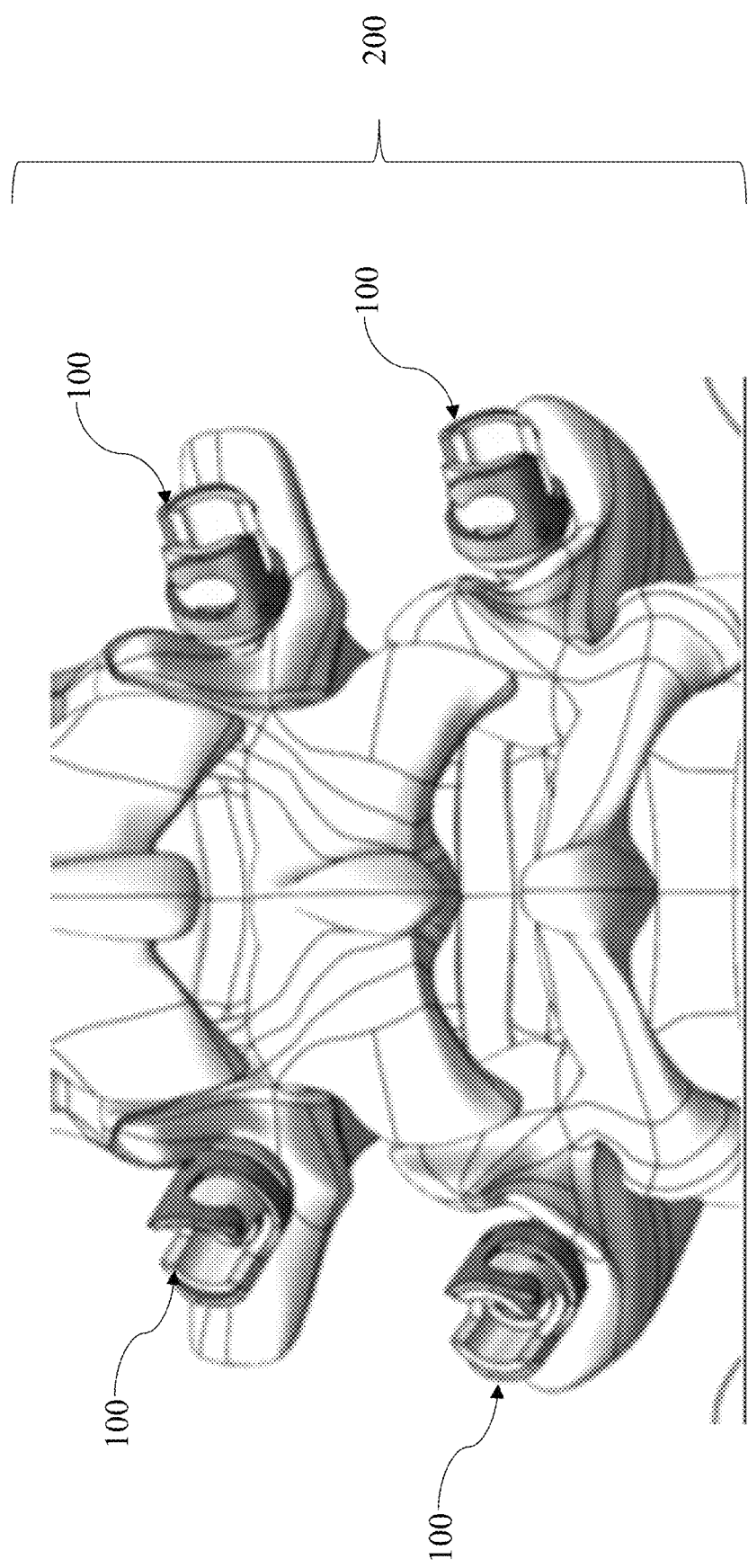
FIG. 29C depicts a perspective view of a pedicle screw system within a spinal segment region and having a tulip assembly in an open position, according to at least some embodiments described herein.

The first embodiment of the pedicle screw system 100 may be placed into the spinal segment region 200 of the patient (as shown in FIG. 29A). As explained supra, the tulip assembly may be rotated to an open position (as depicted in FIG. 29B and FIG. 29C) by use of the driving tool 180. During such rotation, the first reduction channel 116A receives the first pin 114A and the second reduction channel 116B receives the second pin 114B. The first reduction channel 116A and the second reduction channel 116B are horizontal channels that allow the first pin 114A and the second pin 114B, respectively, to freely turn within the first reduction channel 116A and the second reduction channel 116B, respectively. The rotation to the open position ceases when the first pin 114A is in the extreme position 119 within the first reduction channel 116A. Upon rotation of the tulip assembly to the open position, the receiving chamber 151 of the tulip body 102 and the access opening 103 of the tulip ring 108 align such that the receiving chamber 151 and the access opening 103 receive the coupling saddle 106 and the cylindrical rod 110 (as shown in FIG. 29D).

Figure 29D:
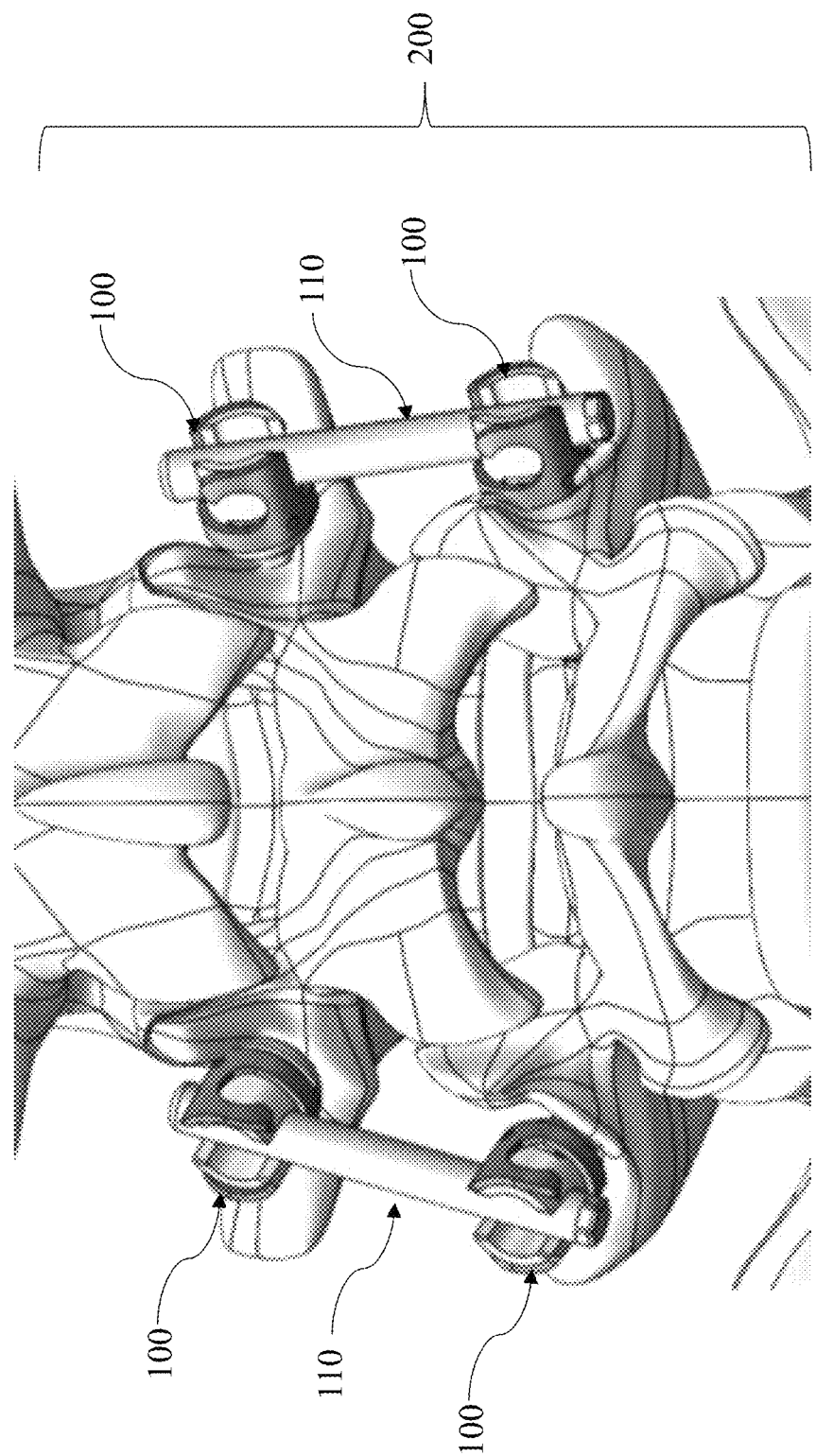
FIG. 29D depicts a perspective view of a pedicle screw system within a spinal segment region and having a tulip assembly in an open position such that a cylindrical rod may be received therein, according to at least some embodiments described herein.
Figure 29E:
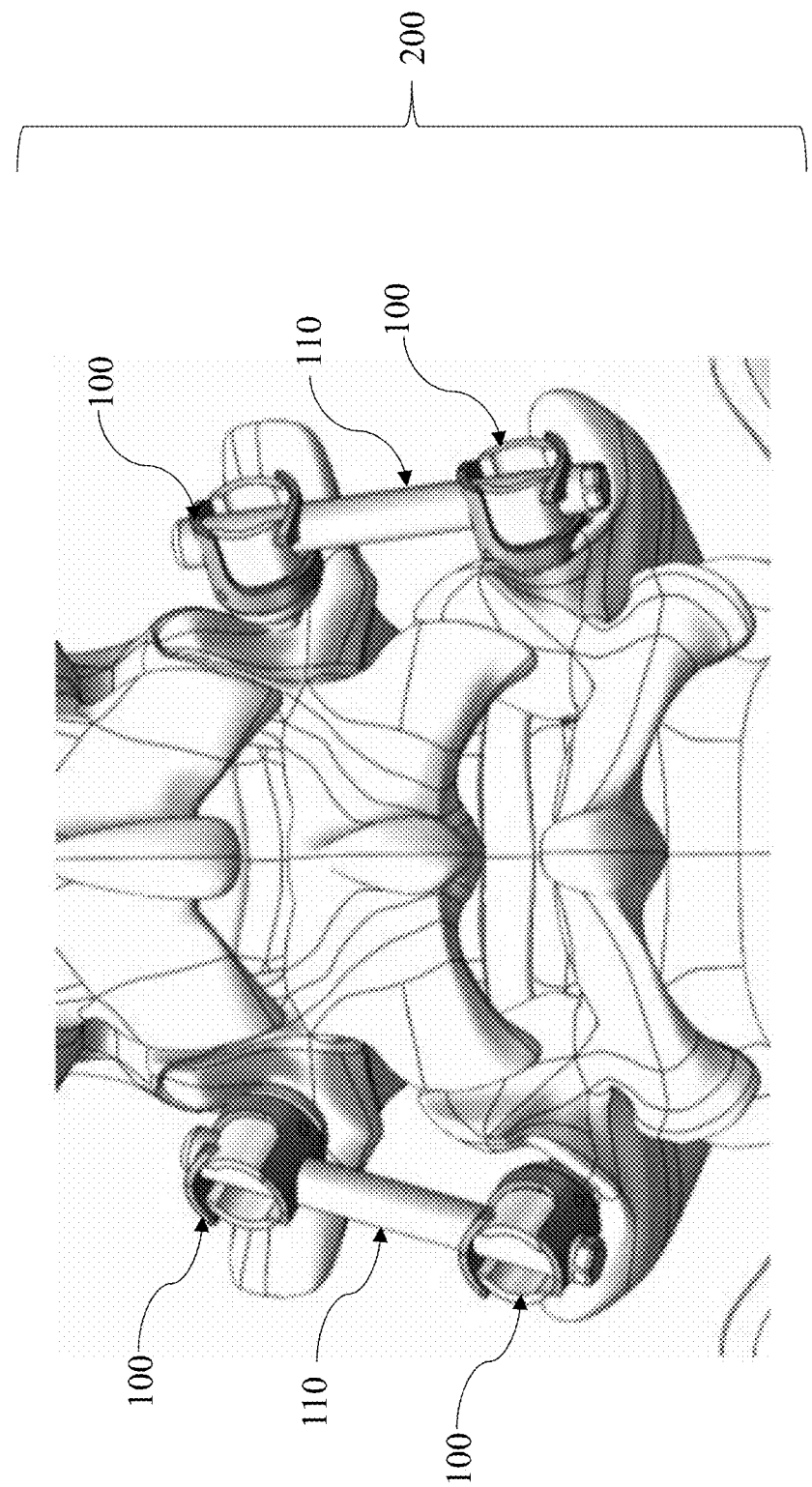
FIG. 29E depicts a perspective view of a pedicle screw system within a spinal segment region and having a tulip assembly in a closed position after receiving cylindrical rod therein, according to at least some embodiments described herein.

As shown in FIG. 29D and FIG. 29E, typically two systems of the first embodiment of the pedicle screw system 100 may be inserted into respective vertebrae and adjusted to distract and/or stabilize the spinal column. However, it should be appreciated that any quantity of the first embodiment of the pedicle screw system 100 may be used based on the needs of the patient.

As explained supra, an axial downward force may be imparted or applied on the cylindrical rod 110 when the tulip assembly is in the open position. When such action occurs, the coupling saddle 106 moves within the tulip assembly and is pushed against the substantially spherical head portion 105A of the pedicle screw 104 to secure the pedicle screw 104. Moreover, upon imparting the axial downward force on the cylindrical rod 110 when the tulip assembly is in the open position and rotating the tulip assembly to a closed position, the cylindrical rod 110 is configured to contact a sidewall of the tulip body 102, the first incline plane 111A imparts a downward force on the cylindrical rod 110, and the second incline plane 111B imparts a downward force on the cylindrical rod 110. The downward force that the first incline plane 111A and the second incline plane 111B impart on the cylindrical rod 110 is a retention force on the cylindrical rod 110 that secures the cylindrical rod 110 in place as seated against the coupling saddle 106 within the tulip assembly. Specifically, as a result of the axial downward force exerted on the cylindrical rod 110, an interference fit is created such that the cylindrical rod 110 is secured within the tulip assembly and the tulip assembly is secured at an angle relative to the pedicle screw 104.

Moreover, as a result of the axial downward force exerted on the cylindrical rod 110 when the tulip assembly is in the open position and rotating the tulip assembly to the closed position, the first pin 114A leaves the first reduction channel 116A and approaches the first ramp down portion 116E (as shown in FIG. 4) and the second pin 114B leaves the second reduction channel 116B and approaches the second ramp down portion (not shown). As an illustrative example, when the first pin 114A approaches the ramp down portion 116E, axial force applies pressure of the cylindrical rod 110. A final portion of the first securement portion 116C (as shown in FIG. 4) is located opposite the extreme position 119. The final portion of the first securement portion 116C captures and secures the first pin 114A (as shown in FIG. 6 and FIG. 7). Moreover, the final portion of the first securement portion 116C (as shown in FIG. 4) prevents the first pin 114A from backing out of this final seated position. Similar actions occur for the second pin 114B, as explained infra. Further, the securement of the first pin 114A in the first securement portion 116C and the second pin 114B in the second securement portion 116D locks or secures the pedicle screw system 100 in place. For illustrative purposes, the tulip assembly is depicted in FIG. 8B and FIG. 8C in the closed position without the cylindrical rod 110.

Moreover, when the tulip assembly is in the closed or final position, exertion of another axial downward force on the cylindrical rod 110 is required while rotating the tulip assembly CCW to the open position to release or unsecure the cylindrical rod 110 from the tulip assembly.

Figure 12:
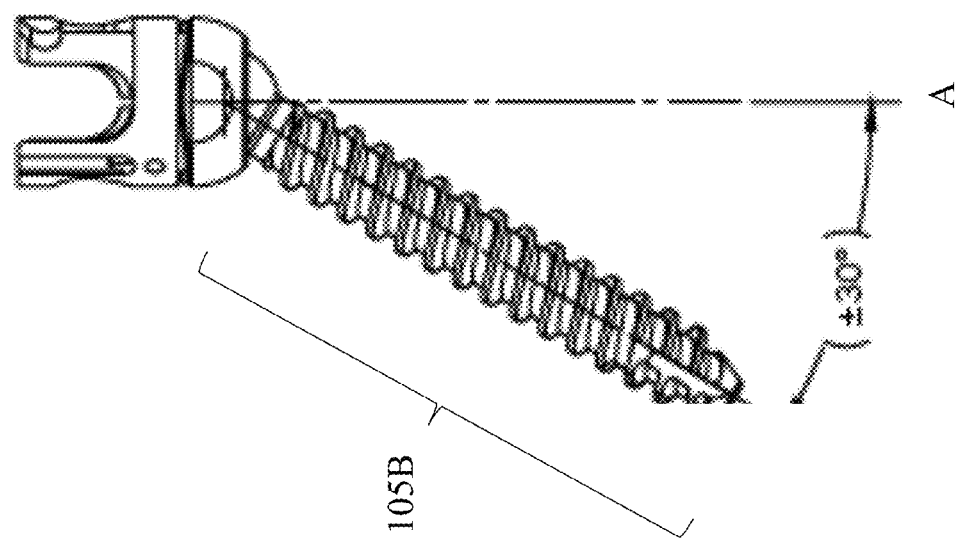
FIG. 12 depicts a perspective view of a second embodiment of a pedicle screw used in a pedicle screw system, according to at least some embodiments described herein.

FIG. 10-FIG. 17 depict a second embodiment of a pedicle screw system 300 and components of the second embodiment of the pedicle screw system 300. Similar to the first embodiment of the pedicle screw system 100, the second embodiment of the pedicle screw system 300, as depicted in at least FIG. 10 and FIG. 11, comprises numerous components, such as the pedicle screw 104 and the tulip assembly (that includes the tulip ring 108 and the tulip body 102). Moreover, the materials comprising the components of the first embodiment of the pedicle screw system 100 are identical to or substantially similar to the materials comprising the components of the second embodiment of the pedicle screw system 300. As shown in FIG. 12, the body portion 105B of the pedicle screw 104 of the second embodiment of the pedicle screw system 300 may move outward from a center of the pedicle screw 104 at an angle up to approximately 30 degrees for ease of insertion within the spinal segment region 200.

Figure 14:
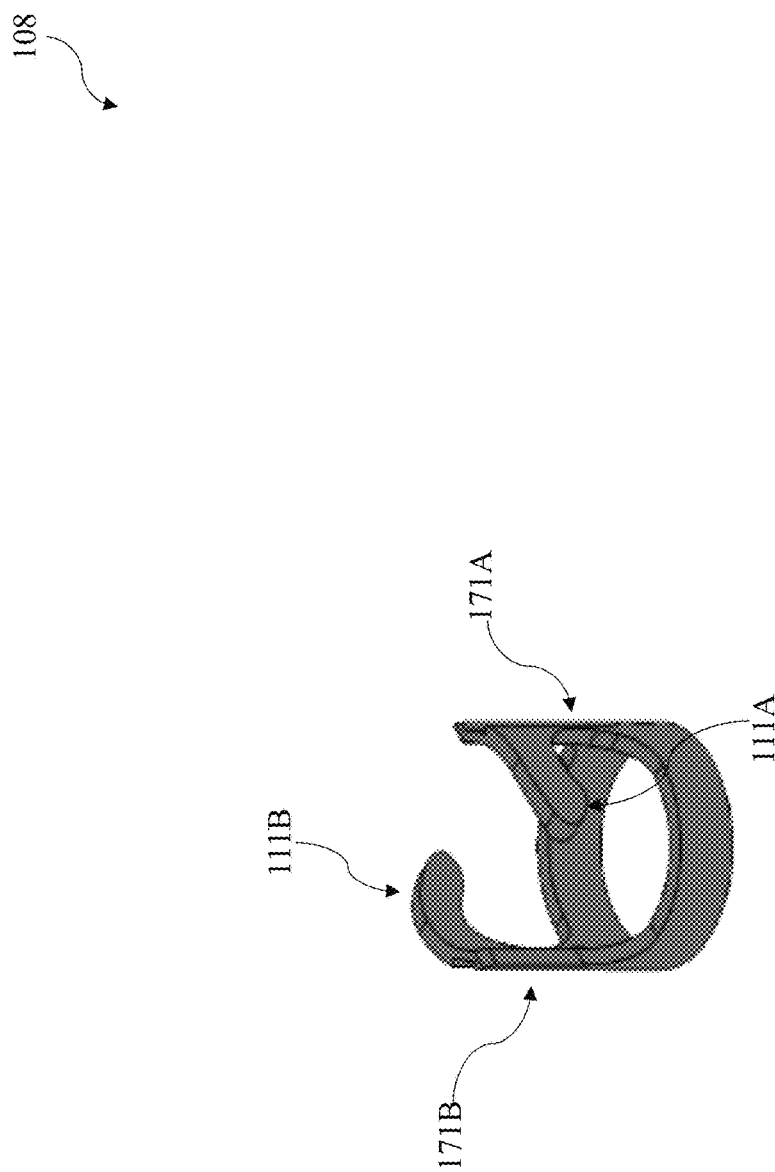
FIG. 14 depicts a perspective view of a tulip ring used in a second embodiment of a pedicle screw system, according to at least some embodiments described herein.

Moreover, the second embodiment of the pedicle screw system 300 may also include the coupling saddle 106, the first pin 114A and the second pin 114B, and a wave spring 204. The first pin 114A and the second pin 114B may be dowel pins, in examples. It should be appreciated that the components of the second embodiment of the pedicle screw system 300 are substantially similar to the components of the first embodiment of the pedicle screw system 100. For example, the tulip ring 108 of the second embodiment of the pedicle screw system 300 (as depicted in FIG. 14) is substantially similar to the tulip ring 108 of the first embodiment of the pedicle screw system 100.

Figure 13A:
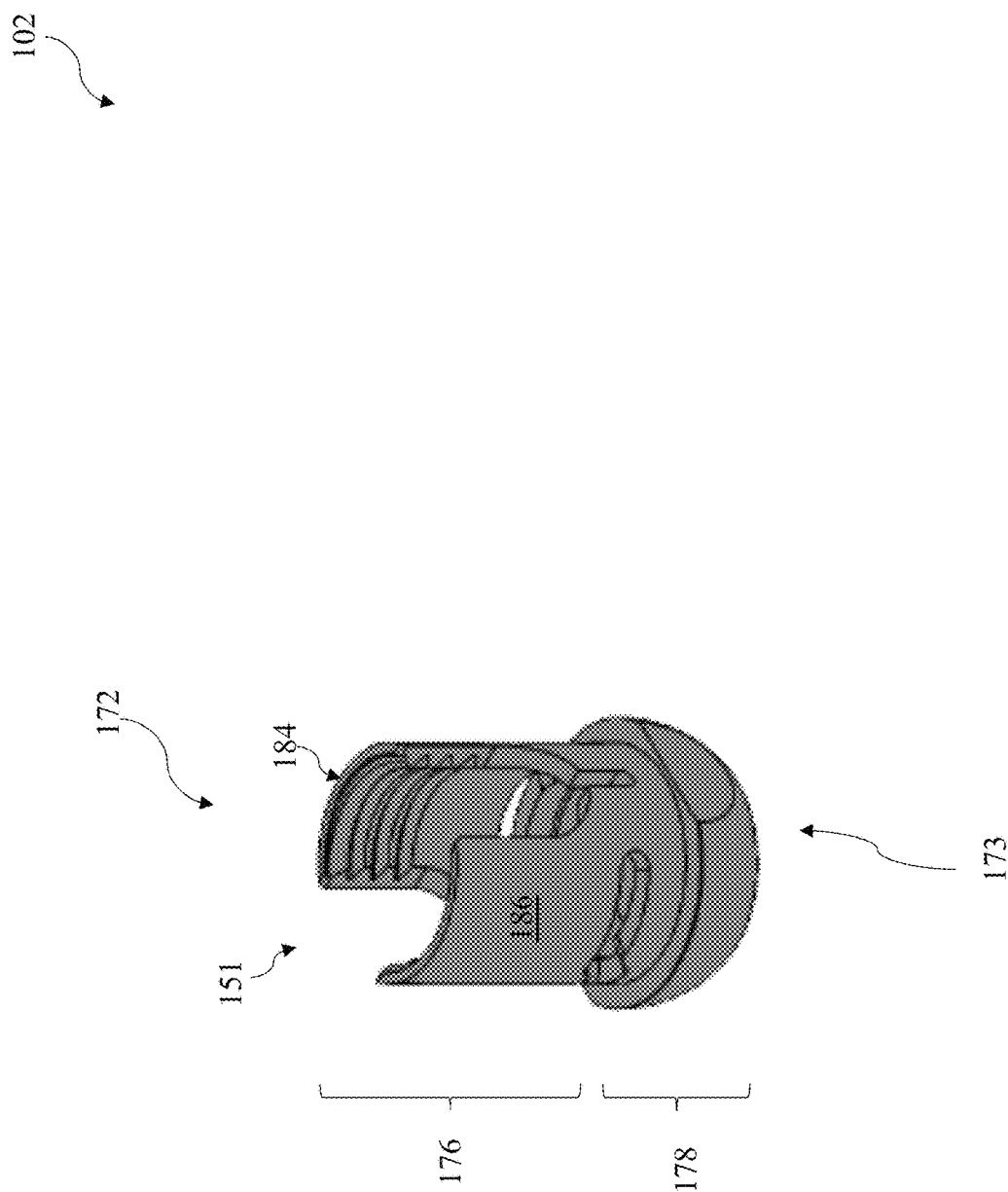
FIG. 13A depicts a perspective view of a tulip body used in a second embodiment of a pedicle screw system, according to at least some embodiments described herein.
Figure 13B:
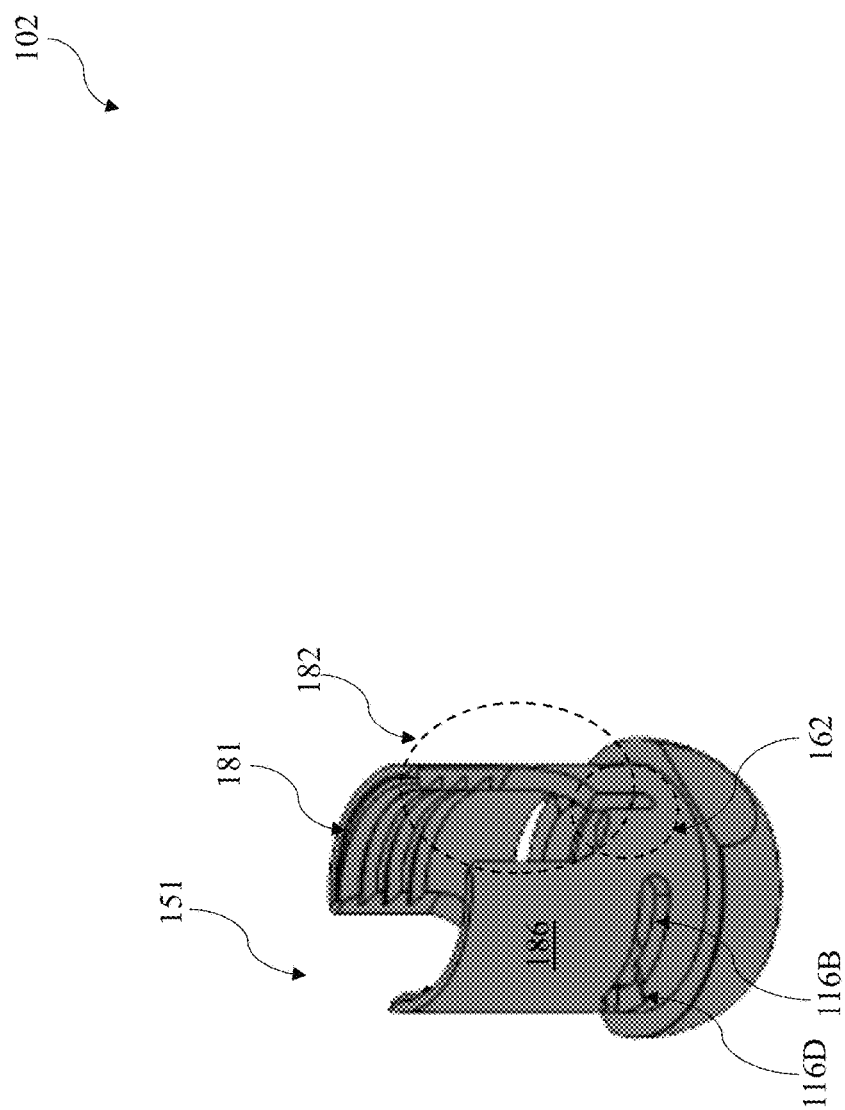
FIG. 13B depicts another perspective view of a tulip body used in a second embodiment of a pedicle screw system, according to at least some embodiments described herein.

Differing from the first embodiment of the pedicle screw system 100, the tulip body 102 of the second embodiment of the pedicle screw system 300, as depicted in at least FIG. 13A and FIG. 13B, includes a body portion 176. The distal end 173 of the tulip body 102 comprises a protrusion section 178 that may be semi-circular in shape. The body portion 176 includes a first portion 184 and a second portion 186. The first portion 184 extends away from the distal end 173 of the tulip body 102 at a first location. The second portion 186 extends away from the distal end 173 of the tulip body 102 at a second location. The first location is disposed opposite the second location. Moreover, a threaded section 181 of FIG. 13B is located in an interior of the first portion 184 proximate the proximal end 172. Further, the threaded section 181 is additionally located in an interior of the second portion 186 proximate the proximal end 172.

Between the first portion 184 and the second portion 186 of the tulip body 102 is a first recess 182 that slopes towards the distal end 173 of the tulip body 102. The first recess 182 is affixed to a first elliptical portion 162 at a third location. The first elliptical portion 162 is located closer to the distal end 173 of the tulip body 102 than the first recess 182. Moreover, the third location is located between the first location of the first portion 184 and the second location of the second portion 186.

Moreover, between the first portion 184 and the second portion 186 of the tulip body 102 is a second recess (not shown) that slopes towards the distal end 173 of the tulip body 102. The second recess is affixed to a second elliptical portion (not shown) at a fourth location. The second elliptical portion is located closer to the distal end 173 of the tulip body 102 than the second recess. Moreover, the fourth location is located between the first location of the first portion 184 and the second location of the second portion 186. Additionally, the third location is disposed opposite the fourth location.

Furthermore, the first portion 184 of the tulip body 102 of the second embodiment of the pedicle screw system 300 also includes a first ramp down portion 116E (not shown) located between the first reduction channel 116A (not shown) and the first securement portion 116C (not shown). The second portion 186 of the tulip body 102 of the second embodiment of the pedicle screw system 300 comprises the second ramp down portion (not shown) located between the second reduction channel 116B and the second securement portion 116D.

Figure 15:
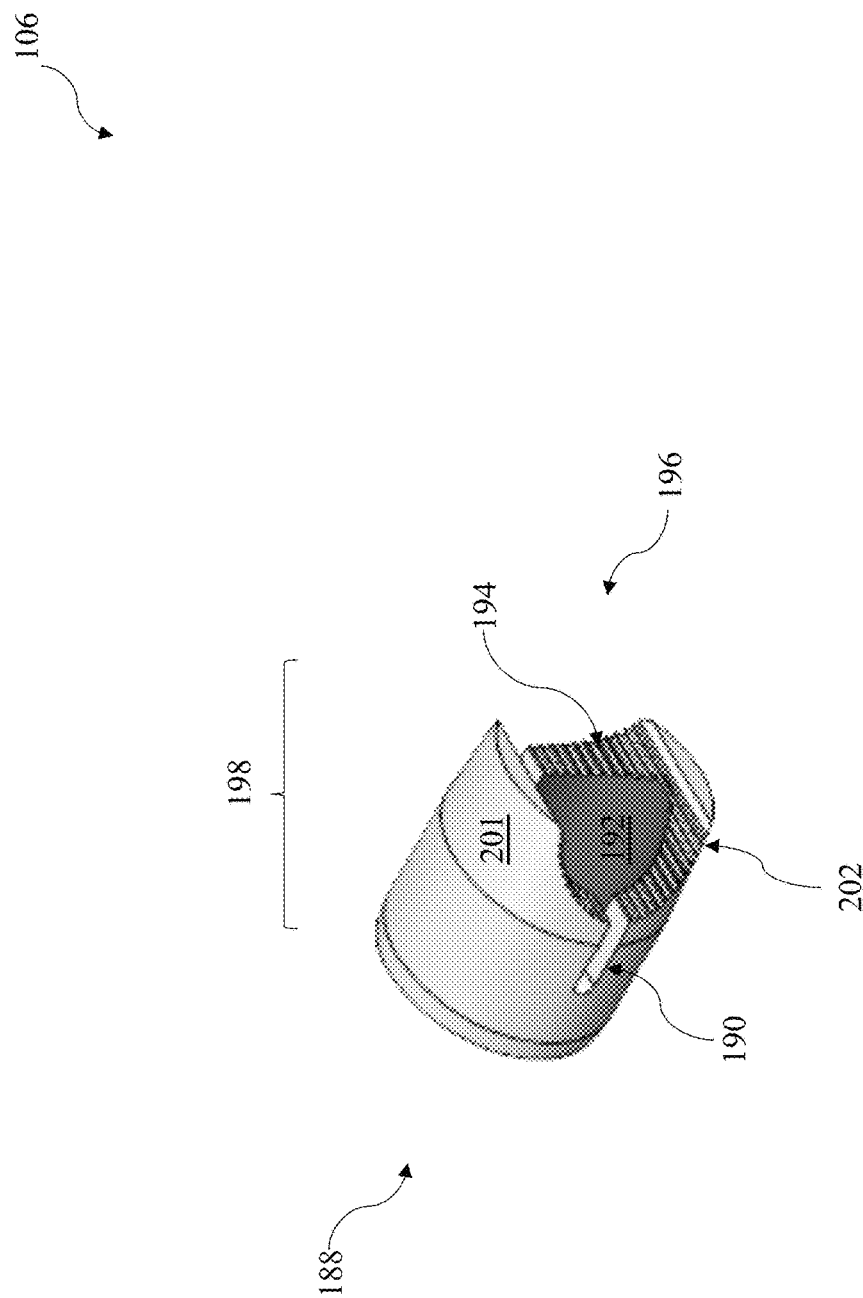
FIG. 15 depicts a perspective view of a coupling saddle used in a second embodiment of a pedicle screw system, according to at least some embodiments described herein.

The coupling saddle 106 of the second embodiment of the pedicle screw system 300 is depicted in at least FIG. 15. The coupling saddle 106 has a body portion 198 and a first end 188 disposed opposite a second end 196. The coupling saddle 106 is generally cylindrical in shape. The body portion 198 of the coupling saddle 106 of the second embodiment of the pedicle screw system 300 includes a rod receiving channel 192, a first extension member 201 extending from a first location on the first end 188 of the coupling saddle 106, and a second extension member 202 extending from a second location on the first end 188 of the coupling saddle 106, where the first location is disposed opposite the second location.

A first recess is formed between the first extension member 201 and the second extension member 202 at a third location and a second recess is formed between the first extension member 201 and the second extension member 202 at a fourth location, where the third location is disposed opposite the fourth location. Furthermore, each of the third location and the fourth location are located between the first location and the second location.

Moreover, the body portion 198 of the coupling saddle 106 of the second embodiment of the pedicle screw system 300 includes an opening located proximate the second end 196. A width of the second end 196 of the coupling saddle 106 is threaded 194 to better grip the cylindrical rod 110.

Additionally, a first elliptical portion 190 is located at the first recess and extends towards the first end 188 of the coupling saddle 106. A second elliptical portion (not shown) is located at the second recess and extends towards the first end 188 of the coupling saddle 106.

Figure 16:
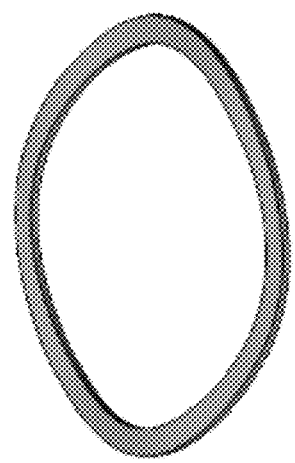
FIG. 16 depicts a perspective view of a wave spring used in a second embodiment of a pedicle screw system, according to at least some embodiments described herein.
Figure 17:
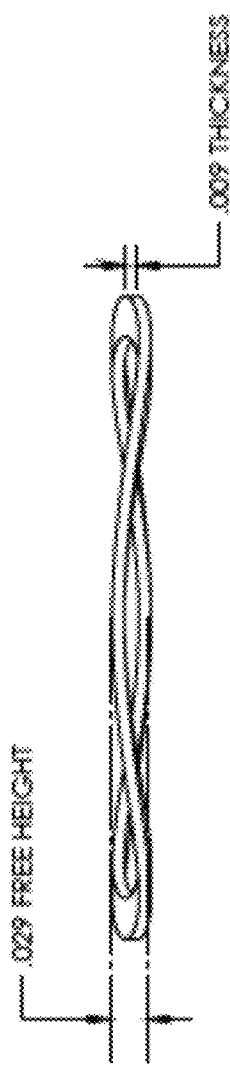
FIG. 17 depicts a side view of a wave spring used in a second embodiment of a pedicle screw system, according to at least some embodiments described herein.
Figure 18:
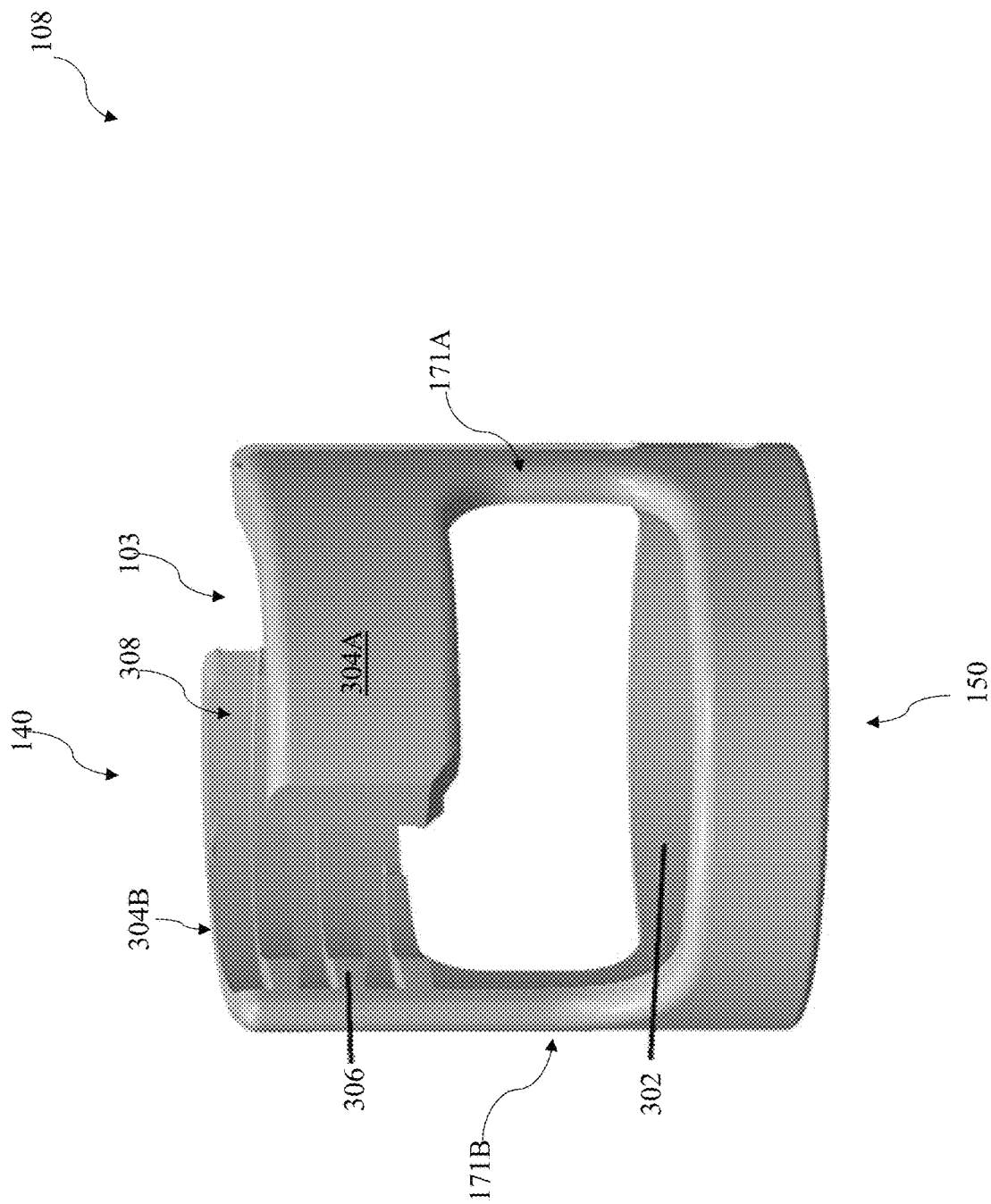
FIG. 18 depicts a perspective view of a tulip ring used in a third embodiment of a pedicle screw system, according to at least some embodiments described herein.
Figure 19A:
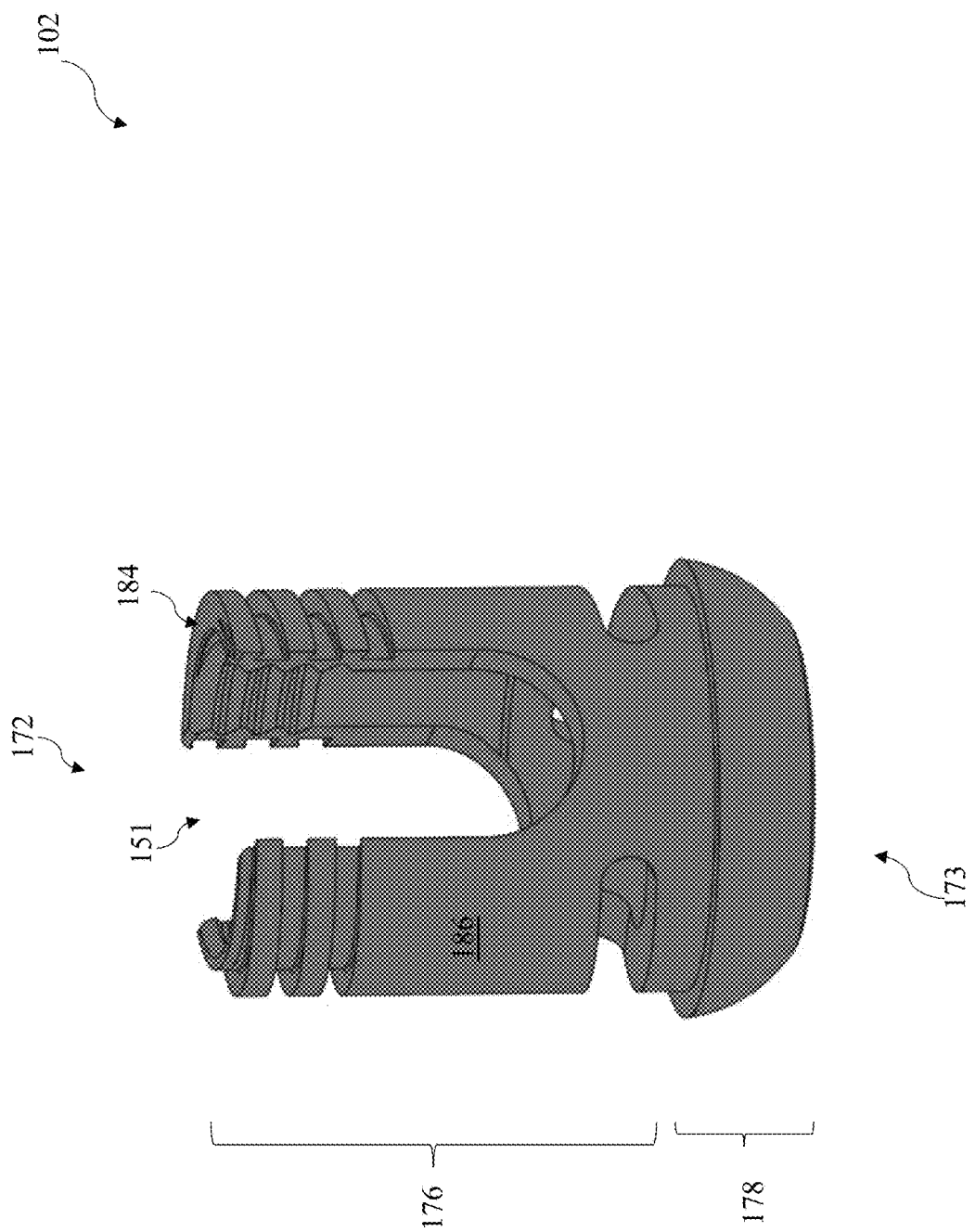
FIG. 19A and FIG. 19B depict perspective views of a tulip body used in a third embodiment of a pedicle screw system, according to at least some embodiments described herein.
Figure 19B:
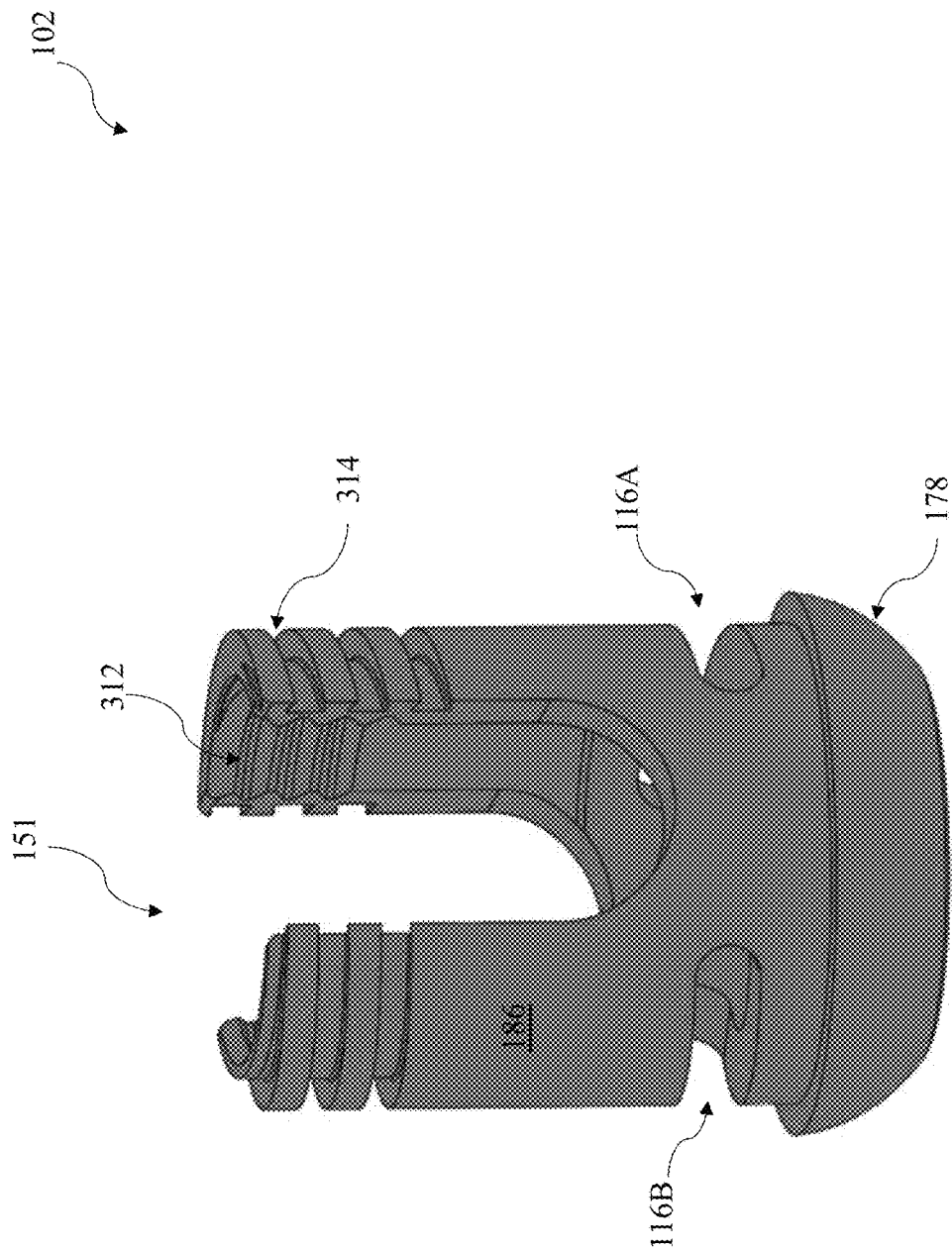

The second embodiment of the pedicle screw system 300 also includes the wave spring 204, as depicted in at least FIG. 16 and FIG. 17. The wave spring 204 is substantially circular in shape and has an opening disposed in a center of the wave spring 204. The wave spring 204 is not planar in shape and includes a free height of approximately 0.029 mm and a thickness of approximately 0.009 mm.

It should be appreciated that the second embodiment of the pedicle screw system 300 functions similarly to the first embodiment of the pedicle screw system 100. For example, the driving tool 180 may be used to secure the second embodiment of the pedicle screw system 300 into the spinal segment region 200 (as shown in FIG. 29A-FIG. 29E) of the patient. Additionally, the method to secure the first embodiment of the pedicle screw system 100 into the bone of the patient at the desired location is similar to the method to secure the second embodiment of the pedicle screw system 300 into the bone of the patient at the desired location.

It should be appreciated that the numerous components of the second embodiment of the pedicle screw system 300 may be affixed together to form the second embodiment of the pedicle screw system 300 in the following way. First, the substantially spherical head portion 105A of the pedicle screw 104 is inserted into the receiving chamber 151 of the tulip body 102. Next, the coupling saddle 106 is pressed into the receiving chamber 151 of the tulip body 102 so the first elliptical portion 162 of the tulip body 102 lines up with the first elliptical portion 190 of the coupling saddle 106 and the second elliptical portion of the tulip body 102 lines up with the second elliptical portion of the coupling saddle 106. Then, the wave spring 204 is passed over the tulip body 102. Next, the tulip ring 108 is passed over the tulip body 102. The first pin 114A and the second pin 114B are pressed through openings in tulip ring 108.

FIG. 18-FIG. 23 depict components of a third embodiment of a pedicle screw system 400. The components of the third embodiment of the pedicle screw system 400 function similarly to the components of the first embodiment of the pedicle screw system 100 and the components of the second embodiment of the pedicle screw system 300.

The tulip ring 108 of the third embodiment of a pedicle screw system 400, as depicted in FIG. 18, FIG. 20, FIG. 21, FIG. 22, and FIG. 23, includes the proximal end 140 disposed opposite the distal end 150. The distal end 150 of the tulip assembly may be configured to receive and secure the substantially spherical head portion 105A of the pedicle screw 104 to the tulip assembly.

At the proximal end 140, the tulip ring 108 of the third embodiment of a pedicle screw system 400 comprises the access opening 103, a first plane 304A disposed on a surface of the tulip ring 108 on the first side 171A, and a second plane 304B disposed on a surface of the tulip ring 108 on the second side 171B. The first side 171A is disposed opposite the second side 171B. Threads 306 may be located on an interior (not shown) of the first plane 304A and on an interior 308 of the second plane 304B. In some examples, the threads 306 are tapered threads. Moreover, in some examples, the quantity of the threads 306 is three, as depicted. However, it should be appreciated that the quantity of the threads 306 is not limited to such. It should be appreciated that the threads on the exterior of the tulip body 102 engage threads on an interior of the tulip ring 108 to provide a means to lock the device in a closed position. Moreover, the threads located on the exterior of the tulip body 102 engage the threads located on the interior of the tulip ring 108 to serve as a primary locking mechanism to secure the cylindrical rod 110 in place, where pins 114A, 114B are used to retain the tulip ring 108 and tulip body 102, allowing for roughly 90 degrees of travel.

The distal end 150 of the tulip ring 108 of the third embodiment of a pedicle screw system 400 includes a circular ring 302 having the thru bore 325 (of FIG. 1A) disposed therein. The thru bore 325 is disposed in a center of the circular ring 302. The distal end 150 of the tulip ring 108 is not threaded.

The tulip body 102 of the third embodiment of the pedicle screw system 400 is depicted in at least FIG. 19A, FIG. 19B, FIG. 20, FIG. 21, and FIG. 22 and includes a proximal end 172 disposed opposite a distal end 173. On the distal end 173, the tulip body 102 of the third embodiment of the pedicle screw system 400 includes a protrusion section 178 that may be semi-circular in shape.

The proximal end 172 of the tulip body 102 of the third embodiment of the pedicle screw system 400 includes a body portion 176. The body portion 176 includes a first portion 184 and a second portion 186. The first portion 184 extends away from the distal end 173 of the tulip body 102 at a first location. The second portion 186 extends away from the distal end 173 of the tulip body 102 at a second location. The first location is disposed opposite the second location.

A first recess is located between the first portion 184 and the second portion 186 at a third location. A second recess is located between the first portion 184 and the second portion 186 at a fourth location. The third location is disposed opposite the fourth location. Moreover, each of the third location and the fourth location are disposed between the first location and the second location.

Further, an exterior of each of the first portion 184 and the second portion 186 near the proximal end of the tulip body 102 comprise a threaded section 314. An interior of each of the first portion 184 and the second portion 186 near the proximal end of the tulip body 102 comprise another threaded section 312. It should be appreciated that the quantity of the threads of the threaded section 314 and the threaded section 312 are not limited to any particular number.

Moreover, the first portion 184 of the tulip body 102 of the third embodiment of the pedicle screw system 400 near the distal end 173 comprises the first ramp down portion (not shown) located between the first reduction channel 116A and the first securement portion 116C (not shown). The second portion 186 of the tulip body 102 of the third embodiment of the pedicle screw system 400 near the distal end 173 comprises the second ramp down portion (not shown) located between the second reduction channel 116B and the second securement portion 116D (not shown).

Figure 20:
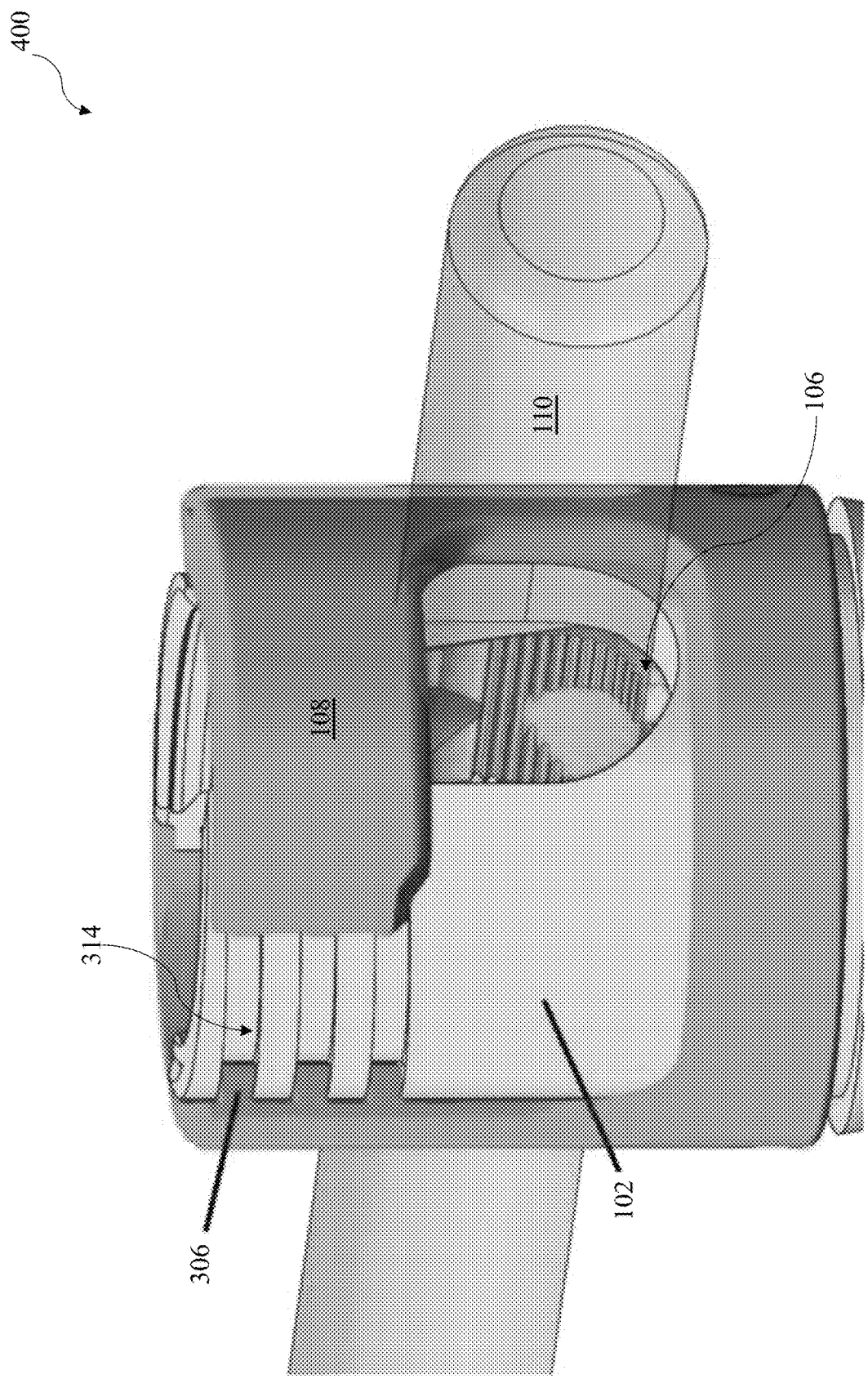
FIG. 20, FIG. 21, and FIG. 22 depict perspective views of a third embodiment of a pedicle screw system, according to at least some embodiments described herein.
Figure 21:
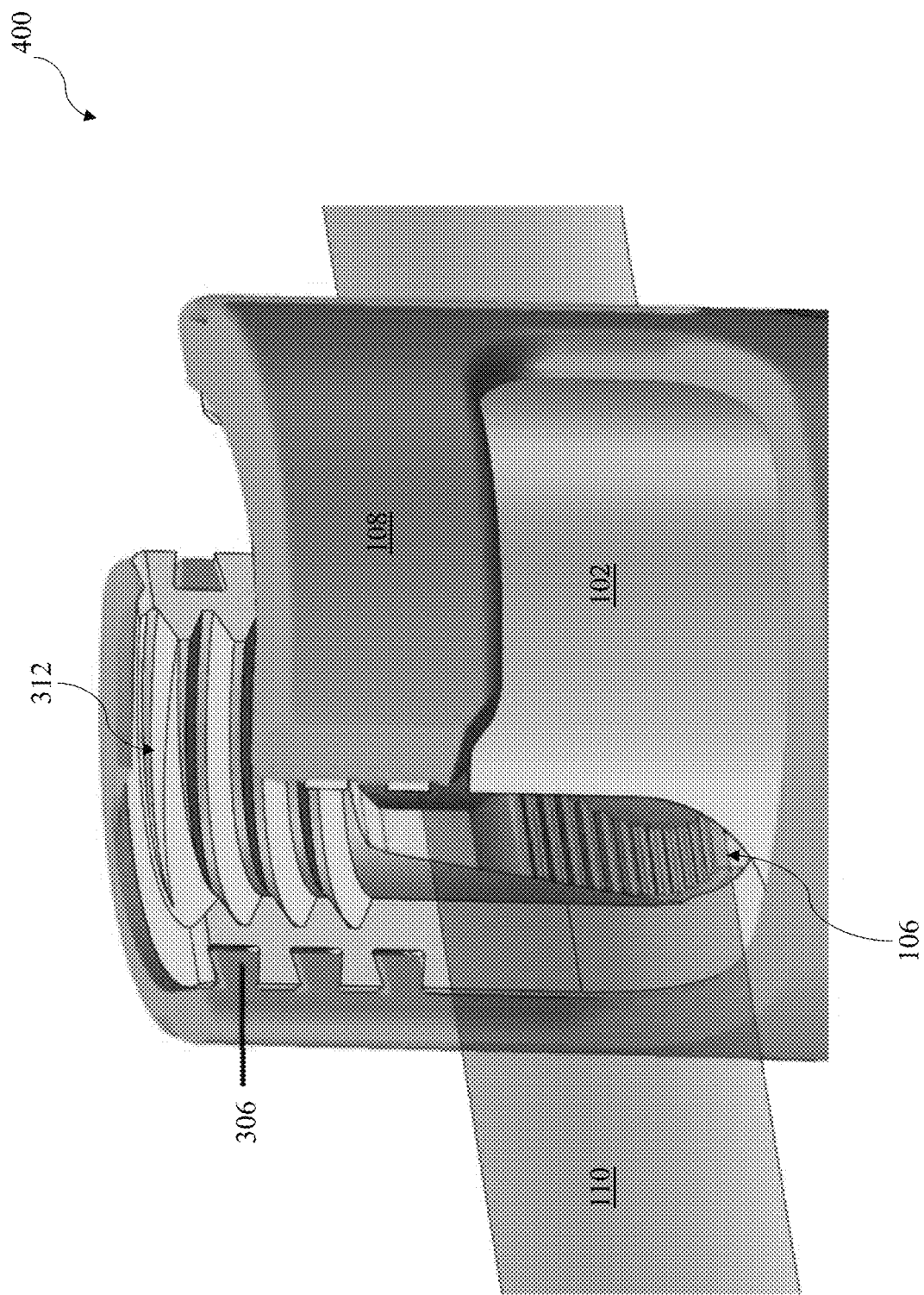
Figure 22:
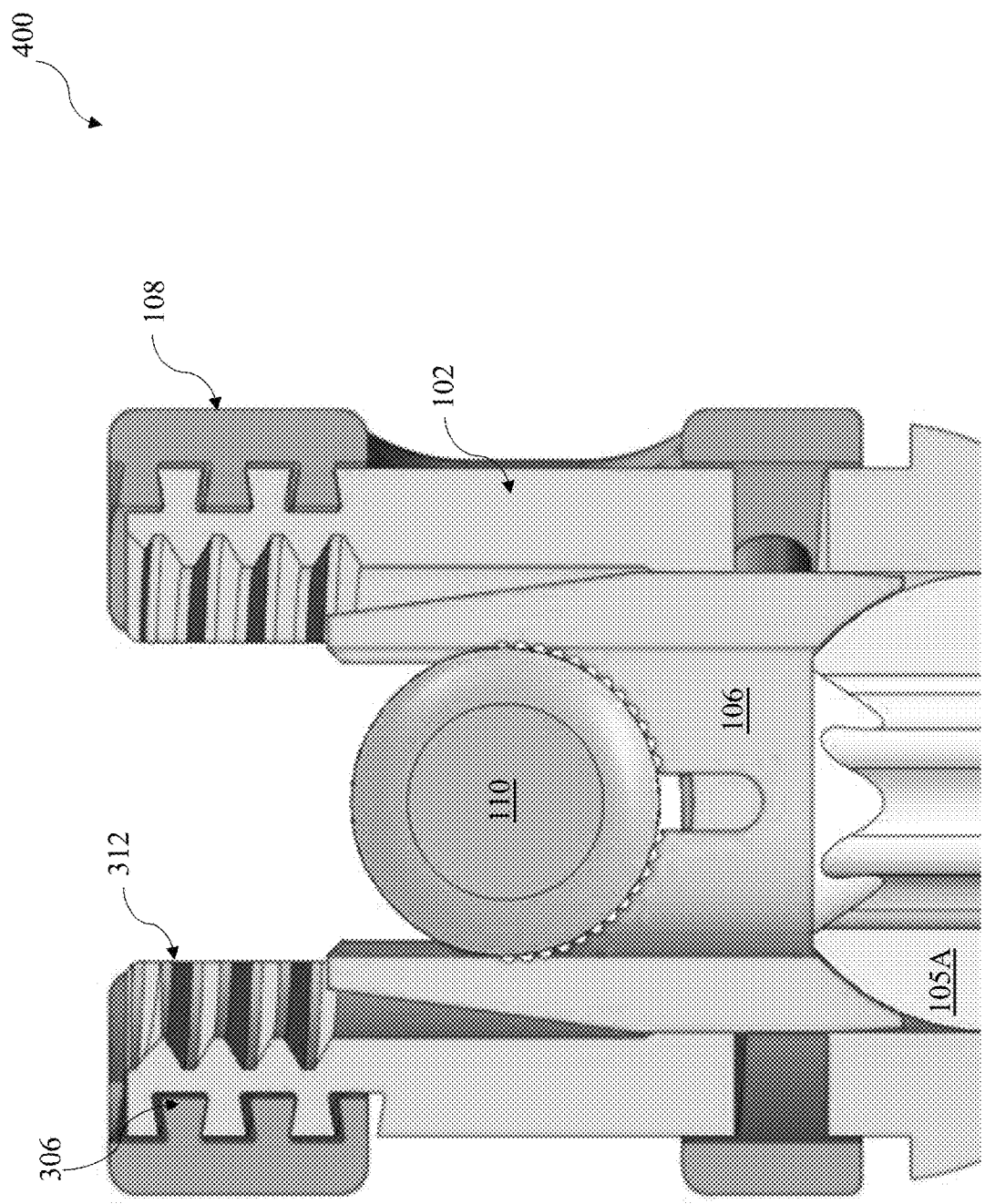
Figure 23:
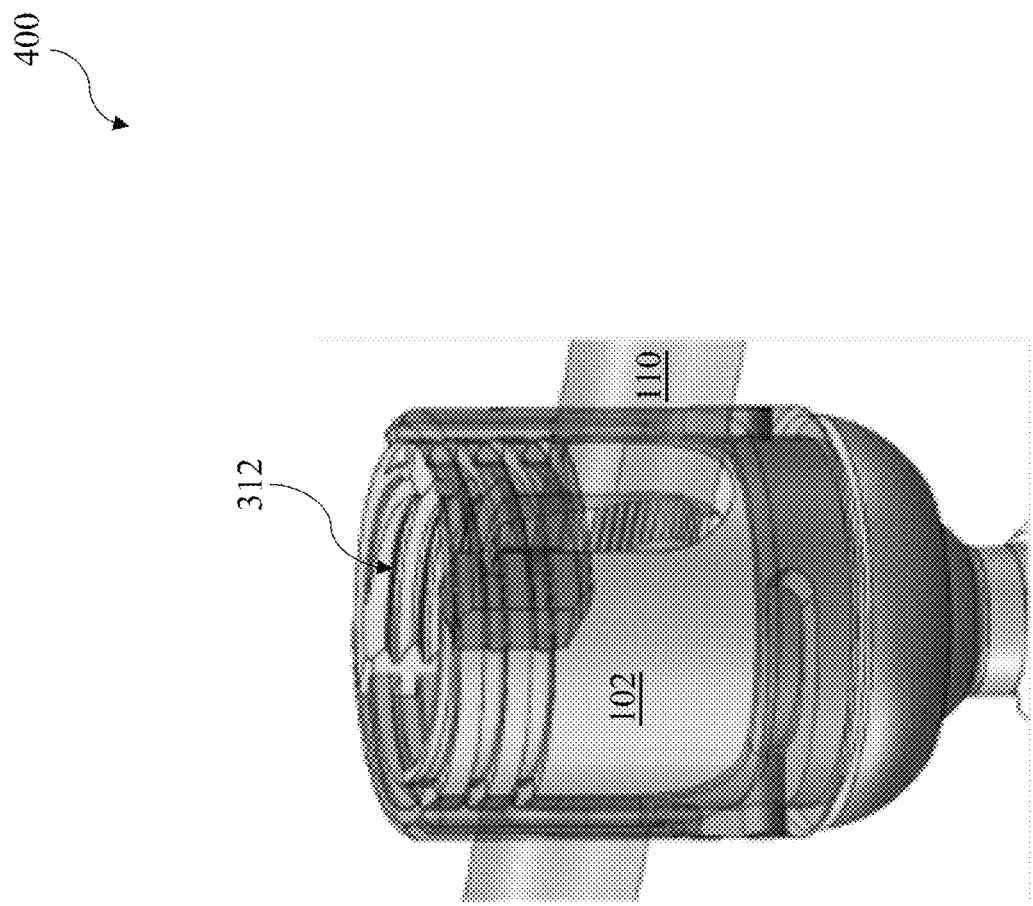
FIG. 23 depicts a perspective view of a third embodiment of a pedicle screw system having components in a locked position, according to at least some embodiments described herein.

As shown in at least FIG. 20, FIG. 21, and FIG. 22, the interior threads 306 of the tulip ring 108 engage the exterior threaded section 314 of the tulip body 102 in an interlocking manner such that the threads cannot be pulled apart from one another. In some examples, the threads 306 of the tulip ring 108 are tapered threads. The interior threading of the tulip ring 108 and the exterior threading of the tulip body 102 eliminate splay and increase the axial preload retained by the pedicle screw 104 in the final locked position.

Figure 24:
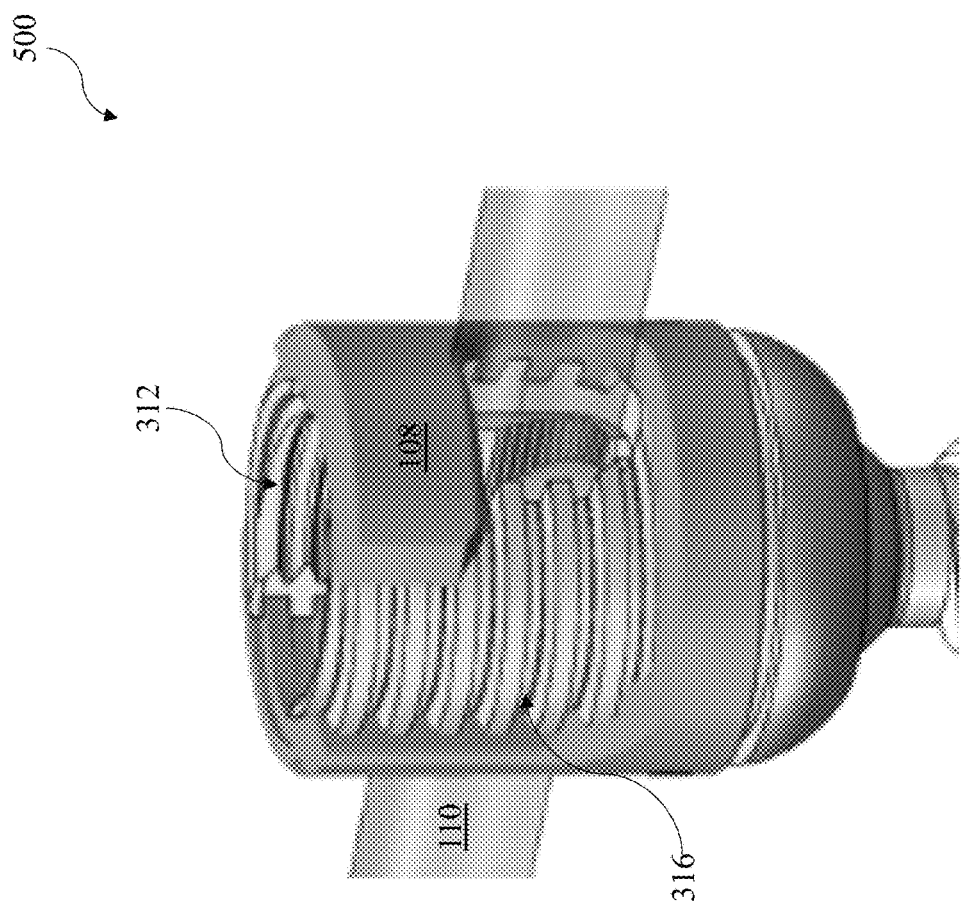
FIG. 24 and FIG. 25 depict perspective views of a tulip body of a fourth embodiment of a pedicle screw system, according to at least some embodiments described herein.
Figure 25:
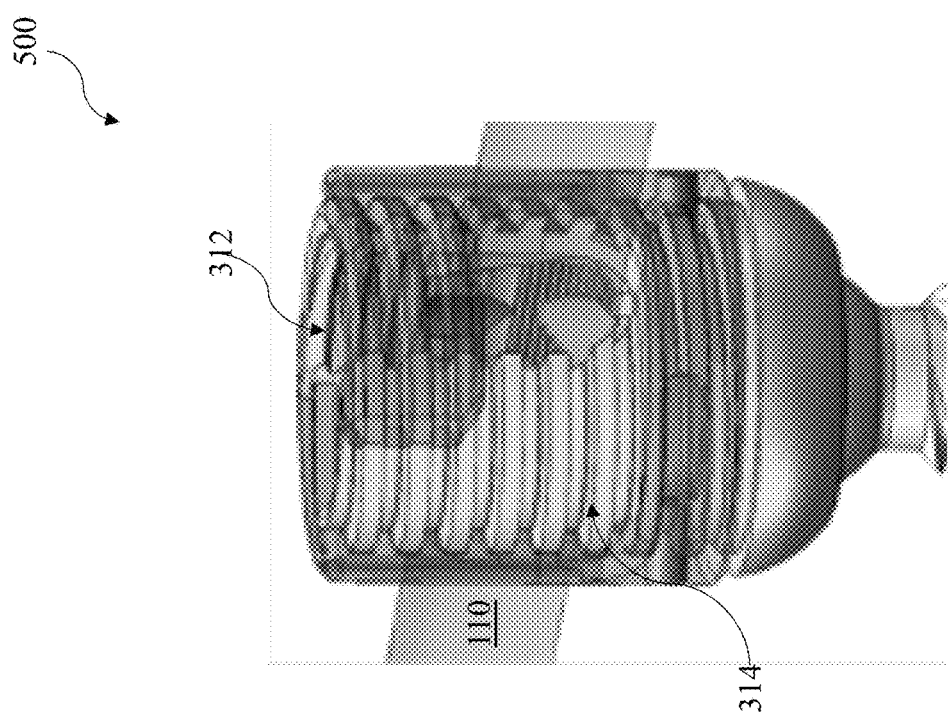
Figure 26:
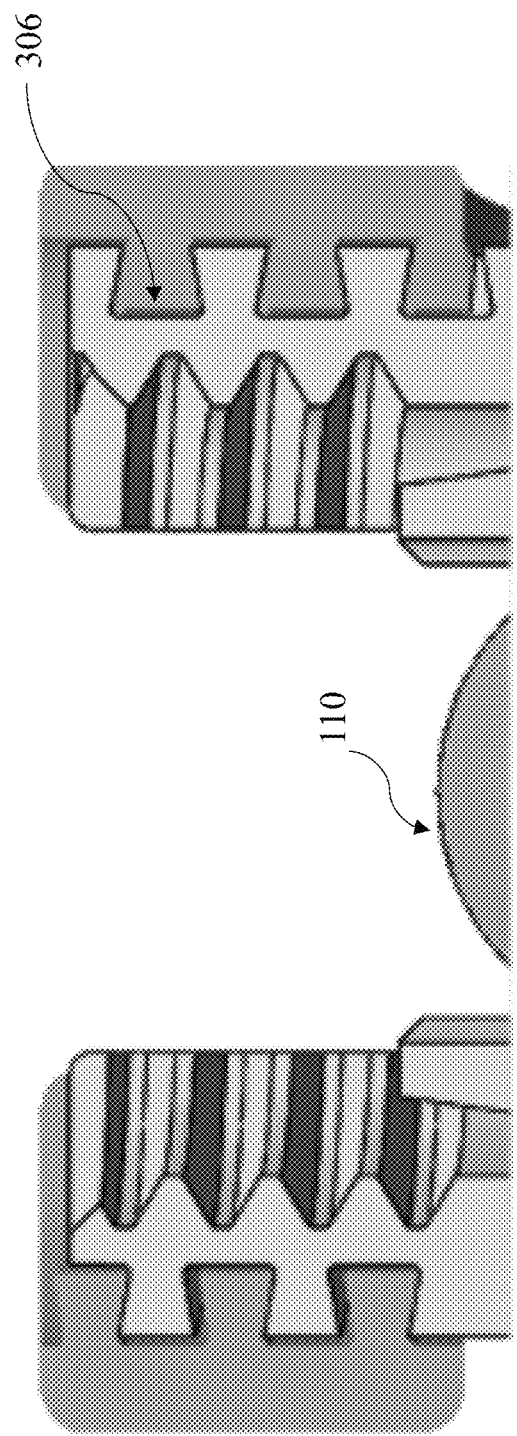
FIG. 26 depicts a side view of a pedicle screw system having tapered threads, according to at least some embodiments described herein.

FIG. 24 and FIG. 25 depict perspective views of the tulip body 102 of a fourth embodiment of a pedicle screw system 500 having an entirety of an exterior of the tulip body 102 comprising threads 316. The threads 316 on the exterior of the tulip body 102 engage threads on an interior of the tulip ring 108 to provide a means to lock the device in a closed position. In particular, the threads 316 on the exterior of the tulip body 102 engage threads on the interior of the tulip ring 108 to provide resistance against deflection upward of the tulip body 102 and during locking of the cylindrical rod 110. Moreover, the threads 316 on the exterior of the tulip body 102 engage the threads on the interior of the tulip ring 108 similarly to a threaded nut and bolt connection. In the locked position of the device, there is a portion of the threads located between the inner and outer tulip that continue to engage to reduce the potential for deflection under the load. FIG. 26 depicts a side view of a pedicle screw system having tapered threads. The tapered threads of FIG. 26 prevent radial splay under load conditions.

When introducing elements of the present disclosure or the embodiments thereof, the articles "a," "an," and "the" are intended to mean that there are one or more of the elements. Similarly, the adjective "another," when used to introduce an element, is intended to mean one or more elements. The terms "including" and "having" are intended to be inclusive such that there may be additional elements other than the listed elements.

Although this invention has been described with a certain degree of particularity, it is to be understood that the present disclosure has been made only by way of illustration and that numerous changes in the details of construction and arrangement of parts may be resorted to without departing from the spirit and the scope of the invention.

What is claimed is:
1. A pedicle screw system comprising:
   a pedicle screw comprising a body portion located at a distal end and affixed to a substantially spherical head portion located at a proximal end of the pedicle screw, wherein the body portion comprises threads configured to penetrate and secure the pedicle screw system within a spinal segment region;
   a coupling saddle;
   a cylindrical rod; and
   a tulip assembly comprising:
      a tulip ring having a proximal end disposed opposite a distal end of the tulip ring,
         the proximal end comprising:
            an access opening;
            a first incline plane disposed on a surface of the tulip ring on a first side;
            a second incline plane disposed on the surface of the tulip ring on a second side, the first side being disposed opposite the second side; and
            a threaded portion located on an interior of the proximal end of the tulip ring; and
         the distal end of the tulip ring comprising:
            a thru bore located in a center of the tulip ring;
            a first pin located on an interior of the first side; and
            a second pin located on an interior the second side; and
      a tulip body having a proximal end disposed opposite a distal end of the tulip body,
         the proximal end comprising:
            a receiving chamber; and
            a threaded portion located on an exterior of the proximal end of the tulip body; and
         the distal end of the tulip body comprising:
            a first ramp down portion located between a first reduction channel and a first securement portion on the first side of the tulip body; and
            a second ramp down portion located between a second reduction channel and a second securement portion on a second side of the tulip body, the first side of the tulip body being disposed opposite the second side of the tulip body; and
      wherein the threaded portion on the interior of the proximal end of the tulip ring engages the threaded portion on the exterior of the proximal end of the tulip body to lock the pedicle screw system, and
      wherein upon rotation of the tulip assembly to an open position, the receiving chamber of the tulip body and the access opening of the tulip ring align such that the receiving chamber and the access opening receive the coupling saddle and the cylindrical rod and the first and the second reduction channel receive the first and the second pin, respectively.
2. The pedicle screw system of claim 1, wherein the thru bore is configured to receive a portion of the substantially spherical head portion of the pedicle screw therethrough.

3. The pedicle screw system of claim 1, wherein the coupling saddle is cylindrical in shape and has a proximal end disposed opposite a distal end of the coupling saddle, and wherein the coupling saddle comprises:
a main body defining a rod receiving channel;
one or more extensions proximally protruding from the main body; and
an inner bore formed on the distal end of the main body for coupling the substantially spherical head portion of the pedicle screw.

4. The pedicle screw system of claim 1, wherein by imparting a downward force on the cylindrical rod when the tulip assembly is in the open position, the coupling saddle is pushed against the substantially spherical head portion of the pedicle screw to secure the tulip body at an angle relative to the pedicle screw.

5. The pedicle screw system of claim 1, wherein upon imparting an axial downward force on the cylindrical rod when the tulip assembly is in the open position and rotating the tulip assembly to a closed position, the cylindrical rod contacts a sidewall of the tulip body and the first and the second incline plane impart a downward force on the cylindrical rod such that:
the cylindrical rod is secured within the tulip body,
the tulip assembly is secured at an angle relative to the pedicle screw,
the first pin passes the first ramp down portion such that a final portion of the first securement portion captures and secures the first pin in a final locked position, and
the second pin passes the second ramp down portion such that a final portion of the second securement portion captures and secures the second pin in the final locked position.

6. The pedicle screw system of claim 1,
wherein the first and the second reduction channels are located in a first plane,
wherein the first and the second ramp down portions are located in a second plane,
wherein the first and the second securement portions are substantially spherical in shape and are located in a third plane,
wherein the second plane is located between the first and the third planes, and
wherein the third plane is located distally from the first plane.

7. The pedicle screw system of claim 1, wherein the distal end of the body portion of the pedicle screw is cannulated.

8. The pedicle screw system of claim 1, wherein the body portion of the pedicle screw contains one or more fenestrations located between the threads.

9. The pedicle screw system of claim 1, wherein the thru bore of the tulip ring comprises an inner wall configured to secure the substantially spherical head portion of the pedicle screw.

10. The pedicle screw system of claim 1, wherein the cylindrical rod is a straight rod comprising a single diameter.

11. The pedicle screw system of claim 1, wherein a proximal end of the substantially spherical head portion of the pedicle screw comprises driving features.

12. The pedicle screw system of claim 11, wherein a driving tool is configured to engage the driving features of the substantially spherical head portion of the pedicle screw to place and secure the pedicle screw system into the spinal segment region.

13. The pedicle screw system of claim 12, wherein the spinal segment region includes pedicles of a L4-L5 spinal segment region.

14. A tulip assembly configured for use in a pedicle screw system, the tulip assembly comprising:
a tulip ring having a proximal end disposed opposite a distal end,
the proximal end comprising:
an access opening;
a first incline plane disposed on a surface of the tulip ring on a first side;
a second incline plane disposed on the surface of the tulip ring on a second side, the first side being disposed opposite the second side; and
a threaded portion located on an interior of the proximal end; and
the distal end comprising:
a thru bore located in a center of the tulip ring;
a first pin located on an interior of the first side; and
a second pin located on an interior the second side; and
a tulip body having a proximal end disposed opposite a distal end of the tulip body,
the proximal end of the tulip body comprising:
a receiving chamber; and
a threaded portion located on an exterior of the proximal end of the tulip body; and
the distal end of the tulip body comprising:
a first ramp down portion located between a first reduction channel and a first securement portion on a first side of the tulip body; and
a second ramp down portion located between a second reduction channel and a second securement portion on a second side of the tulip body, the first side of the tulip body being disposed opposite the second side of the tulip body; and
wherein the threaded portion on the interior of the proximal end of the tulip ring engages the threaded portion on the exterior of the proximal end of the tulip body to lock the pedicle screw system, and
wherein upon rotation of the tulip assembly to an open position, the receiving chamber of the tulip body and the access opening of the tulip ring align such that the receiving chamber and the access opening receive a coupling saddle and a cylindrical rod and the first and the second reduction channel receive the first and the second pin, respectively.

15. The tulip assembly of claim 14, wherein the cylindrical rod is selected from the group consisting of: a curved rod comprising two or more diameters and a straight rod comprising a single diameter.

16. The tulip assembly of claim 14, wherein the first incline plane and the second incline plane decrease in incline towards the distal end of the tulip ring.

17. A pedicle screw system comprising:
a pedicle screw comprising a body portion located at a distal end and affixed to a substantially spherical head portion located at a proximal end of the pedicle screw, wherein the body portion comprises threads configured to penetrate and secure the pedicle screw system within a spinal segment region;
a wave spring;
a coupling saddle;
a cylindrical rod; and
a tulip assembly comprising:
a tulip ring having a proximal end disposed opposite a distal end of the tulip ring,
the proximal end of the tulip ring comprising:
an access opening;

a first incline plane disposed on a surface of the tulip ring on a first side;

a second incline plane disposed on the surface of the tulip ring on a second side, the first side being disposed opposite the second side; and a threaded portion located on an interior of the proximal end of the tulip ring; and the distal end of the tulip ring comprising:
a thru bore located in a center of the tulip ring;
a first pin located on an interior of the first side; and
a second pin located on an interior the second side; and a tulip body comprising:
a proximal end disposed opposite a distal end of the tulip body, the distal end of the tulip body comprising a protrusion section; and
a body portion comprising:
a first portion extending away from the distal end of the tulip body at a first location and comprising:
a first ramp down portion located between a first reduction channel and a first securement portion; and
a first threaded section located in an interior of the first portion proximate the proximal end of the tulip body;
a second portion extending away from the distal end of the tulip body at a second location and comprising:
a second ramp down portion located between a second reduction channel and a second securement portion, wherein the first location is disposed opposite the second location; and
a second threaded section located in an interior of the second portion proximate the proximal end of the tulip body;
a first sloped recess affixed to a first elliptical portion at a third location; and
a second sloped recess affixed to a second elliptical portion at a fourth location, wherein the third location is disposed opposite the fourth location, and wherein each of the third location and the fourth location are located between the first location and the second location, wherein a portion the threaded portion of the tulip ring engages the first threaded section of the tulip body and another portion of the threaded portion of the tulip ring engages the second threaded section of the tulip body to lock the pedicle screw system, and wherein upon rotation of the tulip assembly to an open position, a receiving chamber of the tulip body and the access opening of the tulip ring align such that the receiving chamber and the access opening receive a coupling saddle and a cylindrical rod and the first and the second reduction channel receive the first and the second pin, respectively.

18. The pedicle screw system of claim 17, wherein the wave spring comprises a thickness of approximately 0.009 mm.

19. The pedicle screw system of claim 17, wherein the body portion of the pedicle screw is movable outward from a center of the pedicle screw at an angle up to 30 degrees.

20. The pedicle screw system of claim 17, wherein the coupling saddle is cylindrical in shape, and wherein the coupling saddle comprises:
a first end disposed opposite a second end, wherein a width of the second end is threaded for coupling the substantially spherical head portion of the pedicle screw; and
a body portion comprising:
a rod receiving channel;
a first extension member extending from a first location on the first end;
a second extension member extending from a second location on the first end,
wherein the first location is disposed opposite the second location;
a first recess formed between the first extension member and the second extension member at a third location;
a first elliptical portion located at the first recess and extending towards the first end;
a second recess formed between the first extension member and the second extension member at a fourth location, wherein the third location is disposed opposite the fourth location, and wherein each of the third location and the fourth location are located between the first location and the second location;
a second elliptical portion located at the second recess and extending towards the first end; and
an opening located proximate the second end.

\* \* \* \* \*